(12) United States Patent
Mukhtar

(10) Patent No.: US 12,098,997 B2
(45) Date of Patent: Sep. 24, 2024

(54) FRAME AND TESTING SYSTEM FOR FIBER REINFORCED POLYMER BOND TESTING

(71) Applicant: KING FAHD UNIVERSITY OF PETROLEUM AND MINERALS, Dhahran (SA)

(72) Inventor: Faisal Muhammad Mukhtar, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/620,432

(22) Filed: Mar. 28, 2024

(65) Prior Publication Data

US 2024/0241036 A1   Jul. 18, 2024

Related U.S. Application Data

(63) Continuation of application No. 17/687,927, filed on Mar. 7, 2022, now Pat. No. 11,982,614.

(51) Int. Cl.
*G01N 19/04* (2006.01)
*G01N 3/04* (2006.01)
(Continued)

(52) U.S. Cl.
CPC ............ *G01N 19/04* (2013.01); *G01N 3/04* (2013.01); *G01N 3/24* (2013.01); *G01N 33/24* (2013.01);
(Continued)

(58) Field of Classification Search
CPC ............ G01N 19/04; G01N 3/04; G01N 3/24; G01N 2203/0423; G01N 2203/0023;
(Continued)

(56) References Cited

U.S. PATENT DOCUMENTS 4,216,625 A * 8/1980 Jenks .................. B24B 27/0608
451/154
11,906,506 B1 * 2/2024 Ghanadiof ................ G06T 7/90
(Continued)

FOREIGN PATENT DOCUMENTS

CN  105628609 A   6/2016
CN  108645723 A   10/2018
(Continued)

*Primary Examiner* — Jonathan M Dunlap
(74) *Attorney, Agent, or Firm* — Oblon, McClelland, Maier & Neustadt, L.L.P.

(57) ABSTRACT

A loading frame for fiber reinforced polymer (FRP)-concrete bond tests includes a standing guide tower, a base section, and a loading beam. The standing guide tower is perpendicularly mounted to the base section. A testing load is applied to the loading beam when performing a series of FRP-concrete bond tests. A sliding end of the loading beam is positioned into a channel within the standing guide tower allowing the loading beam to be positioned at a preferred height. The engagement between the loading beam and the standing guide tower reduces secondary forces. The loading frame is mobile and may also be used with existing testing devices and systems used to perform the series of FRP-concrete bond tests.

19 Claims, 48 Drawing Sheets

(51) Int. Cl.
  *G01N 3/24*   (2006.01)
  *G01N 33/00*  (2006.01)
  *G01N 33/24*  (2006.01)

(52) U.S. Cl.
  CPC . *G01N 33/0003* (2024.05); *G01N 2203/0023* (2013.01); *G01N 2203/0025* (2013.01); *G01N 2203/0091* (2013.01); *G01N 2203/0252* (2013.01); *G01N 2203/0423* (2013.01)

(58) Field of Classification Search
  CPC ... G01N 2203/0025; G01N 2203/0091; G01N 2203/0252; G01N 2203/0003
  See application file for complete search history.

(56) References Cited

U.S. PATENT DOCUMENTS

| | | | | |
|---|---|---|---|---|
| 2006/0117866 | A1* | 6/2006 | Myers | G01N 3/32 |
| | | | | 73/837 |
| 2019/0241414 | A1* | 8/2019 | Willard | B66C 1/22 |
| 2022/0063908 | A1* | 3/2022 | Buel | B66F 9/07 |

FOREIGN PATENT DOCUMENTS

| | | | | |
|---|---|---|---|---|
| CN | 109580389 | A | | 4/2019 |
| CN | 109612847 | A | | 4/2019 |
| CN | 106840917 | B | | 7/2019 |
| JP | 3178642 | U | * | 9/2012 |
| WO | WO-2015073893 | A1 | * | 5/2015 ........... G01L 5/0052 |

* cited by examiner

FRAME AND TESTING SYSTEM FOR FIBER REINFORCED POLYMER BOND TESTING

CROSS-REFERENCE TO RELATED APPLICATIONS

The present application is a Continuation of U.S. application Ser. No. 17/687,927, now allowed, having a filing date of Mar. 7, 2022.

U.S. application Ser. No. 16/530,543 titled "Universal debonding test apparatus for carbon fiber reinforced polymer—concrete system and method for sequential multi-testing" and having a filing date of Aug. 2, 2019 names inventors in common with the present disclosure and is incorporated herein by reference in its entirety.

BACKGROUND

Field of the Invention

The present disclosure relates to a system and method for testing a bond between fiber-reinforced polymer (FRP) and concrete. More specifically, the present disclosure describes an adaptable loading frame that may be used in FRP-concrete bond testing.

Description of the Related Art

Fiber reinforced polymer (FRP) is a construction, maintenance and/or repair technique used to strengthen concrete structures that may have lost capacity and/or deteriorated with time. FRP applications may also be used to address changes in the service life of a concrete structure.

Even though FRP techniques are successful in strengthening concrete structures, with time bond degradation may occur between the FRP and the corresponding concrete structure. Generally, bond degradation occurs in the form of premature debonding between FRP and concrete and undermines an intended design capacity for the FRP strengthened system. Therefore, to improve FRP strengthened systems, debonding behavior is generally analyzed in laboratory conditions and in situ conditions.

Direct tension pull-off tests are frequently used for in situ bond tests. The double-shear test, the single shear test, the beam-bending type test, and the mixed-mode test are some other tests conducted under laboratory conditions. Generally, a different testing method is used for each of the tests. For example, the testing system and method used for the double-shear test may be different from the testing system and method used for the mixed-mode test. Therefore, the results may vary according to the testing system and method. The lack of a mutual testing method, which can perform all FRP-concrete bond tests, prevents precise interpretation of a FRP-concrete bond.

When technical limitations are applied to existing testing systems, the overall analysis result may vary from an accurate representation of the FRP-concrete bond. Furthermore, certain existing testing methods may not be compatible with some FRP-concrete bonds. As a consequence, the tests results obtained for the FRP-concrete bond using a particular test may lack the interpretative value and information otherwise provided by testing methods that were not utilized.

Existing FRP-concrete bond testing methods utilize unique testing devices, fixing procedures and/or loading systems that differ from one testing method to another. For example, some FRP-concrete bond tests require a fixed-position loading system such as a universal testing machine whereas other testing methods require a mobile loading system.

To eliminate using different testing devices for each test, a convertible testing device that may be used for each of the FRP-concrete bond tests would be beneficial. Furthermore, the testing device may need to be operatively coupled with an existing test apparatus used for FRP-concrete bond tests. In another aspect, the testing device may need to be mobile such that a FRP-concrete test is not limited by location. Mobility allows the testing device to be mechanically engaged with devices that can be, but are not limited to, hydraulic jacks. To further eliminate the need to use different testing devices for different FRP-concrete bond tests, the testing device may need to eliminate secondary forces or reactions that occur during a FRP-concrete bond test. By reducing the secondary forces, the overall accuracy of the FRP-concrete bond test result may be improved.

A testing device that is convertible has been disclosed previously. See F. M. Mukhtar, "Universal debonding test apparatus for carbon fiber reinforced polymer—concrete system and method for sequential multi-testing," U.S. patent application Ser. No. 16/530,543, incorporated herein by reference in its entirety. The convertibility of the testing device permits application to a majority of the FRP-concrete bond tests with a fixed-position loading machine such as the universal testing machine. Even though convertibility is mentioned, the need for an adaptable loading system, the need for a mobile testing system, and the need for a testing system with high efficiency that reduces secondary reactions are not addressed in the prior art.

In view of the difficulties and drawbacks of existing testing devices, in one aspect, the present disclosure describes a mobile loading system used for testing FRP-concrete bonds. In particular, the use of the loading system described in the present disclosure is not limited by the location of a FRP-concrete bond. In another aspect, the loading system described in the present disclosure may be operatively coupled with different existing testing devices used for FRP-concrete bond testing. Hence, the loading system described in the present disclosure may also be used with the previously disclosed universal test apparatus to perform other FRP-concrete bond tests. The loading system of the present disclosure may be used with a hydraulic jack and the universal test apparatus of the prior art to perform in situ direct tension pull-off tests on an actual structure. In a further aspect, the loading system described in the present disclosure reduces the effect and the presence of secondary actions and/or reactions such that externally applied loads are effectively utilized to test a FRP-concrete bond. Thus, the efficiency of the results obtained for the FRP-concrete bond may improve.

SUMMARY OF THE INVENTION

The present disclosure describes a loading frame that may be used for loading purposes when performing a series of fiber reinforced polymer (FRP)-concrete bond tests. In particular, the loading frame described in the present disclosure may be configured to perform a double-shear test for a FRP-concrete bond, a single-shear test for a FRP-concrete bond, a mixed-mode test for a FRP-concrete bond, a beam-bending type test with a FRP-concrete bond, or a direct tension pull-off test for a FRP-concrete bond. In an aspect of the loading frame described in the present disclosure, the loading frame may also be used to perform sequential multi-testing, wherein the double-shear test, the single-shear test, the direct tension pull-off test, and the beam-bending type test are sequentially performed.

The loading frame may also be configured to be used with existing testing devices and loading devices which may be, but is not limited to, a hydraulic jack. In another aspect, the loading frame described in the present disclosure provides mobility such that a test from the series of FRP-concrete bond tests may be performed at a preferred location. More specifically, the loading frame of the present disclosure may be used to perform FRP-concrete bond tests in laboratory conditions and in situ conditions. In an aspect of the loading frame described in the present disclosure, secondary forces are reduced such that the overall efficiency of the results obtained for the series of FRP-concrete bond tests may improve.

The loading frame includes a standing guide tower, a base section, and a loading beam. A load required to perform the series of FRP-concrete bond tests is generally applied to the loading beam. A sliding end of the loading beam is slidably positioned along a channel of the standing guide tower. Therefore, a height required for a test from the series of FRP-concrete bond tests may be selected using a plurality of height-adjusting slots of the standing guide tower. The standing guide tower is perpendicularly mounted to the base section. When an existing testing device or system is used with the loading frame of the present disclosure, the existing testing device or system may be positioned on the base section and engaged to the loading beam.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

All illustrations of the drawings are for the purpose of describing selected embodiments of the present disclosure and are not intended to limit the scope of the present disclosure or accompanying claims.

The present disclosure describes an adaptable loading frame that may be used to test a fiber-reinforced polymer (FRP)-concrete bond. In one aspect, the loading frame described in the present disclosure provides mobility for FRP-concrete bond testing. FRP-concrete bond testing at any location is generally restricted with existing fixed-position loading machines. The mobility of the loading frame allows FRP-concrete bond testing to be performed in a location which can be, but is not limited to, a laboratory, a construction site, and a research facility. For example, by utilizing the loading frame of the present disclosure, direct tension pull-off tests may be performed in situ, e.g., where a structure is located, in contrast to being performed in a laboratory environment. In another aspect, the loading frame described in the present disclosure allows FRP-concrete bond testing to be performed in conjunction with existing testing devices and existing loading devices such as hydraulic jacks. In a further aspect, the loading frame described in the present disclosure may be used to perform tension-type tests and compression-type tests. In a further aspect, the loading frame described in the present disclosure may be used to reduce secondary forces and/or secondary reactions that may affect the overall testing result associated with a FRP-concrete bond test.

Figure 1:
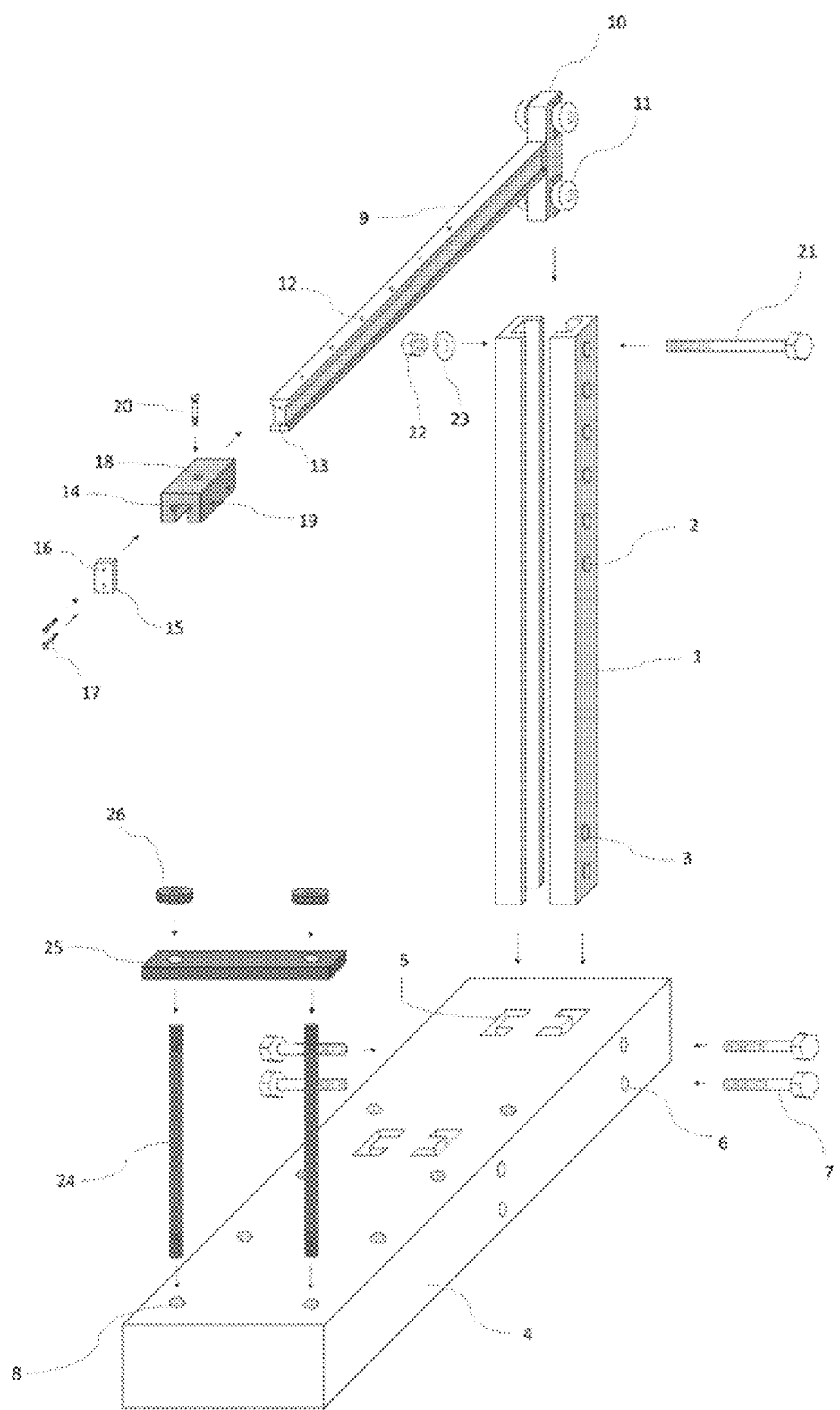
FIG. 1 is a perspective exploded view of the loading frame described in the present disclosure, wherein a standing guide tower, a base section, a loading beam, and a coupling device are illustrated.

As seen in FIG. 1, the loading frame described in the present disclosure comprises a standing guide tower 1, a base section 4, and a loading beam 9. The standing guide tower 1 is used to set a height required for a series of FRP-concrete bond tests which includes a double-shear test, a single shear test, a beam-bending type test, a mixed-mode test, and a direct tension pull-off test. As seen in FIG. 1, the standing guide tower 1 comprises a first tower section 101 and a second tower section 103 having a C-shaped cross section. In further reference to FIG. 1, the first tower section 101 is positioned adjacent the second tower section 103, wherein an orientation of the second tower section 103 is a mirror image of an orientation of the first tower section 101, such that the C-shaped cross section of the first tower section 101 and the second tower section 103 configures a channel 109 in between the first tower section 101 and the second tower section 103. As seen in FIGS. 8A-9B, the base section 4, which is rectangular in shape in a preferred embodiment, is generally used to position a concrete block 40 used in the series of FRP-concrete bond tests is performed. As seen in FIG. 1, to position the standing guide tower 1, which is used to set the height required for the series of FRP-concrete bond tests, the base section 4 comprises a first pair of tower-receiving slots 501 which traverses through a top surface 401 of the base section 4 adjacent to a first end 403 of the base section 4. In reference to FIG. 1, to match the C-shaped cross section of the first tower section 101 and the second tower section 103, each of the first pair of tower-receiving slots 501 is also C-shaped. As illustrated in FIG. 1, by removably positioning a bottom end 105 of the first tower section 101 into a first slot 505 of the first pair of tower-receiving slots 501, and by removably positioning a bottom end 105 of the second tower section 103 into a second slot 507 of the first pair of tower-receiving slots 501, the standing guide tower 1 may be perpendicularly mounted into the base section 4.

Figure 7A:
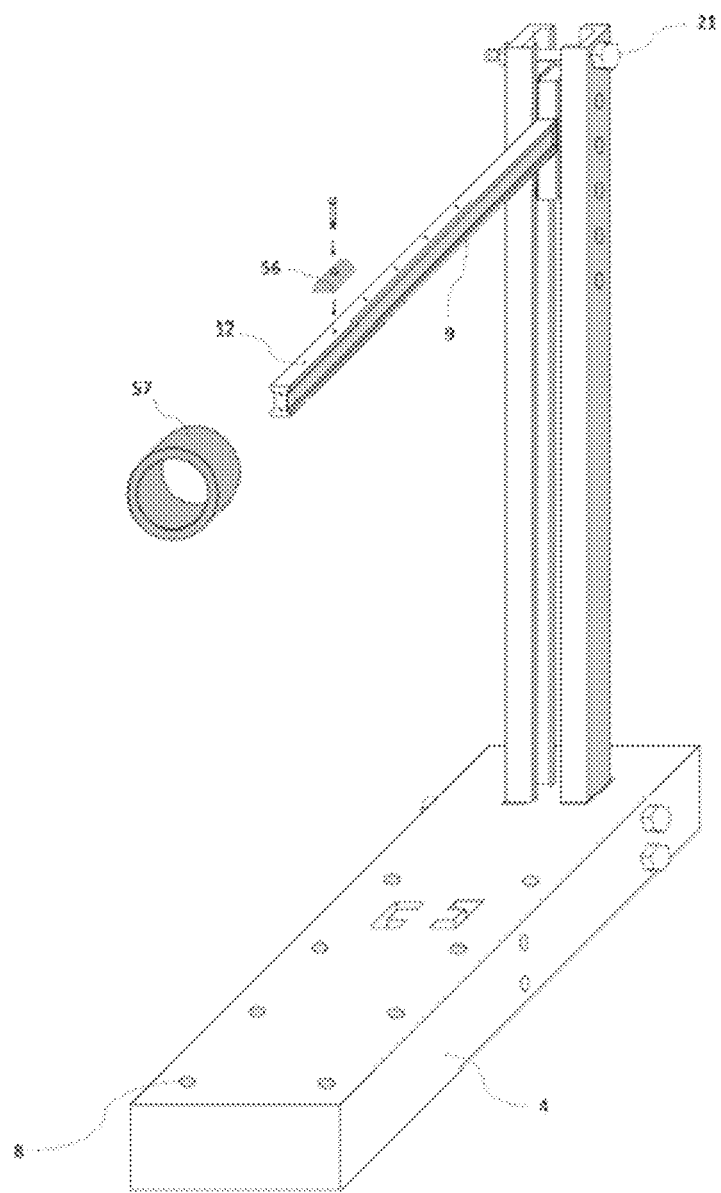
FIG. 7A is a perspective view of the loading frame described in the present disclosure, wherein the coupling device comprises a positioning device and a hollow cylinder from a prior art.
Figure 7B:
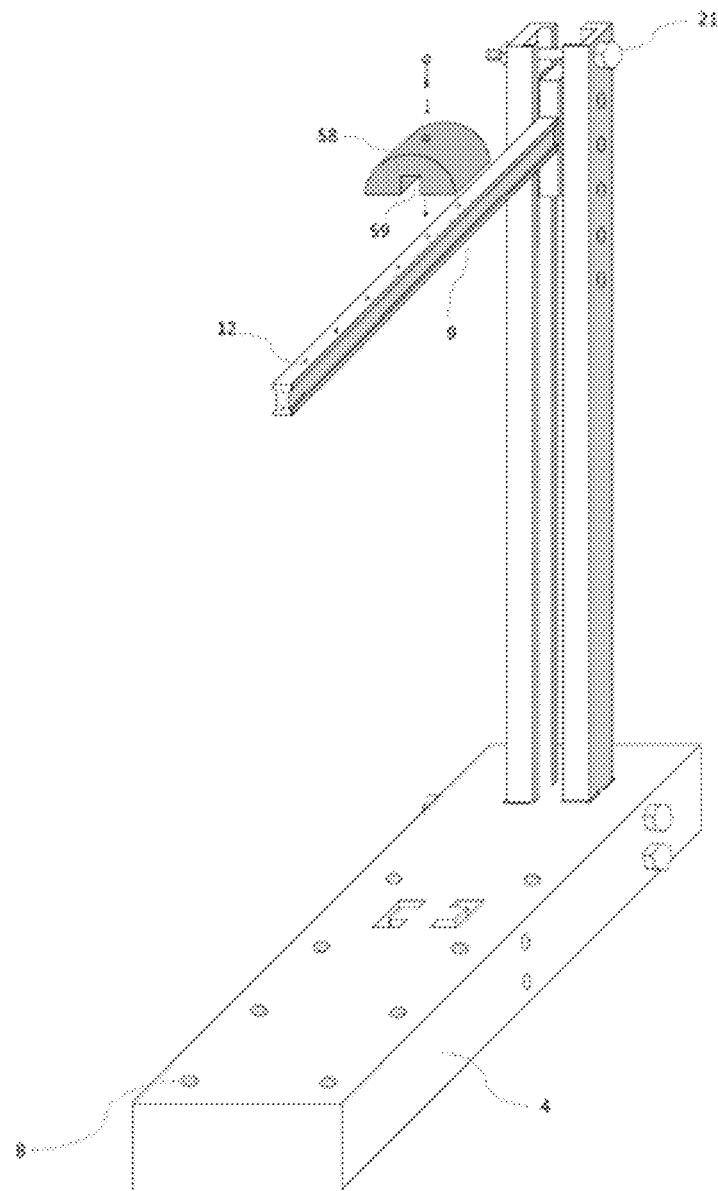
FIG. 7B is a perspective view of the loading frame described in the present disclosure, wherein the coupling device is a semi-cylindrical device from a prior art.
Figure 7C:
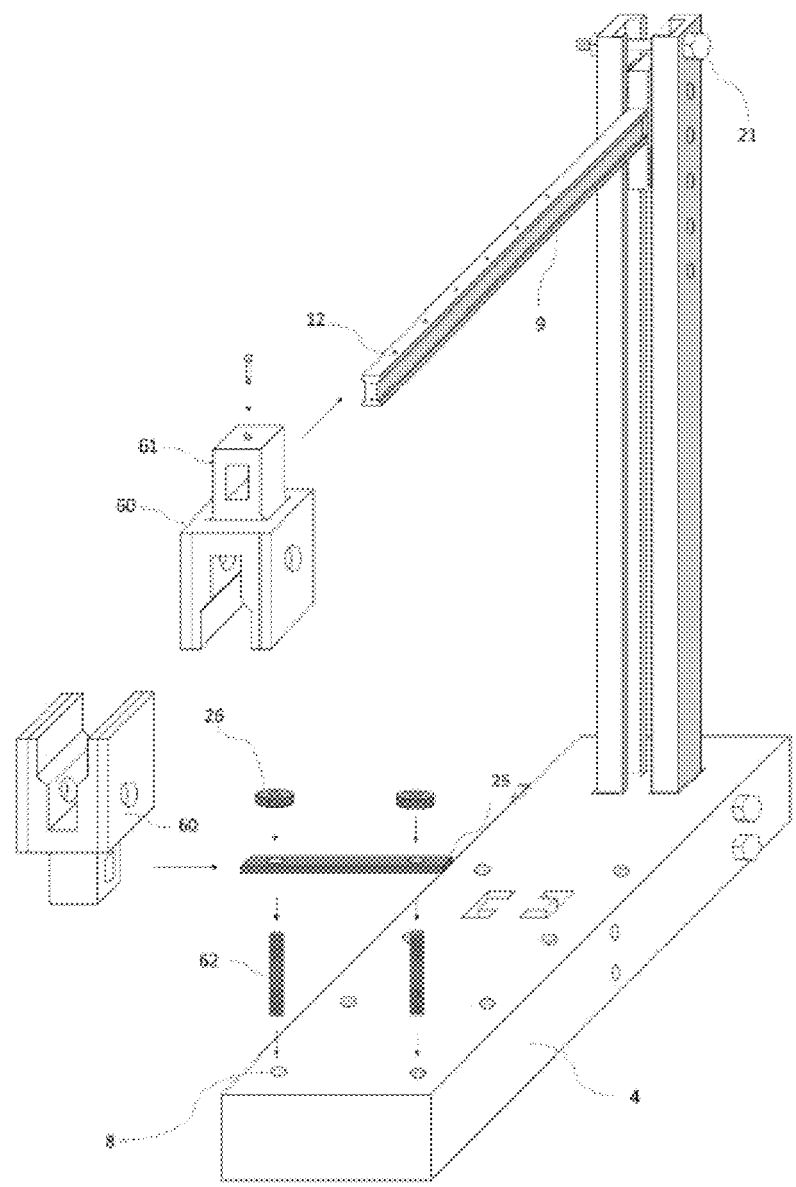
FIG. 7C is a perspective view of the loading frame described in the present disclosure, wherein a prior art consisting of first clamping device and a second clamping device which are used in a double-shear test are illustrated.

Additionally, as seen in FIGS. 7A-7C, the base section 4 further comprises a second pair of tower-receiving slots 503 which traverses the top surface 401 of the base section 4 in between the first end 403 and a second end 405 of the base section 4, wherein a distance from the first end 403 to the second end 405 determines a length of the base section 4. Preferably, referring to FIGS. 7A-7C, the second pair of tower-receiving slots 503 centrally traverses the top surface 401 of the base section 4, and is used to perpendicularly mount the standing guide tower 1 to the base section 4 based on the FRP-concrete bond test that is being performed. Moreover, the second pair of tower-receiving slots 503, seen in FIG. 1 and FIGS. 7A-7C, may also be used to reduce secondary forces/reactions that may occur with the use of different testing devices and thus, increase efficiency. Moreover, as seen in FIG. 1, each of the second pair of tower-receiving slots 503 is also C-shaped to match the C-shaped cross section of the first tower section 101 and the second tower section 103. In particular, similar to the engagement between the standing guide tower 1 and the base section 4 as shown in FIGS. 7A-7C, a bottom end 105 of the first tower section 101 may also be removably positioned into a first slot 505 of the second pair of tower-receiving slots 503 and a bottom end 105 of the second tower section 103 may be removably positioned into a second slot 507 of the second pair of tower-receiving slots 503 such that the standing guide tower 1 is perpendicularly mounted to the base section 4.

As illustrated in FIG. 1 and FIGS. 7A-7C, when the standing guide tower 1 is mounted to the base section 4 at the first pair of tower-receiving slots 501, to secure the first tower section 101 against the base section 4, the loading frame described in the present disclosure comprises a first pair of fasteners 70. In particular, as seen in FIG. 1, the first pair of fasteners 70 is threaded into a first pair of base-traversing fastener holes 601 and a first pair of tower-traversing fastener holes 301 which are concentrically aligned to each other when the bottom end 105 of the first tower section 101 is mounted into the first slot 505 of the first pair of tower-receiving slots 501. As seen in FIG. 1, to insert the first pair of fasteners 70, the first pair of base-traversing fastener holes 601 traverses through a first lateral surface 407 of the base section 4 and into the first pair of tower-receiving slots 501. As further illustrated in FIG. 1, when the bottom end 105 of the first tower section 101 is inserted into the first slot 505, the first pair of fasteners 70 may be positioned through the first pair of base-traversing fastener holes 601 and into the first pair of tower-traversing fastener holes 301 which traverses the first tower section 101 adjacent the bottom end 105.

As seen in FIG. 1 and FIGS. 7A-7C, when the standing guide tower 1 is mounted to the base section 4 at the first pair of tower-receiving slots 501, to secure the second tower section 103 against the base section 4, the loading frame described in the present disclosure comprises a second pair of fasteners 71. In particular, as seen in FIG. 1, the second pair of fasteners 71 is threaded into a second pair of base-traversing fastener holes 603 and a second pair of tower-traversing fastener holes 303 which are concentrically aligned to each other when the bottom end 105 of the second tower section 103 is mounted into the second slot 507 of the first pair of tower-receiving slots 501. In further reference to FIG. 1, to insert the second pair of fasteners 71, the second pair of base-traversing fastener holes 603 traverses through a second lateral surface 409 of the base section 4 and into the first pair of tower-receiving slots 501, wherein the second lateral surface 409 is positioned opposite the first lateral surface 407 such that a distance between the first lateral surface 407 and the second lateral surface 409 determines a width of the base section 4. As illustrated in FIG. 1, when the bottom end 105 of the second tower section 103 is inserted into the second slot 501, the second pair of fasteners 71 may be positioned through the second pair of base-traversing fastener holes 603 and into the second pair of tower-traversing fastener holes 303 which traverses the second tower section 103 adjacent the bottom end 105. In a different embodiment, referring to FIG. 1, the first pair of fasteners 70 and the second pair of fasteners 71 may also be used to secure the standing guide tower 1 with the base section 4 when the standing guide tower 1 is mounted at the second pair of tower-receiving slots 503 in an arrangement similar to as shown in FIG. 1. As illustrated in FIG. 1, a third pair of base-traversing fastener holes 605 and a fourth pair of base-traversing fastener holes 607 may be used.

In particular, as seen in FIG. 1, the third pair of base-traversing fastener holes 605 may traverse the first lateral surface 407 and be aligned with the second pair of tower-receiving slots 503. Thus, in a different embodiment, when the first tower section 101 of FIG. 1 is mounted to the first slot 505 of the second pair of tower-receiving slots 503, the first pair of fasteners 70 may be inserted through the third pair of base-traversing fastener holes 605 and into the first pair of tower-traversing holes 301 to secure the first tower section 101 with the base section 4. In a preferred embodiment, as seen in FIG. 1, the first pair of base-traversing fastener holes 601 and the third pair of base-traversing fastener holes 605 are distributed along the first lateral surface 407 of the base section 4. As further illustrated in FIG. 1, the second pair of base-traversing fastener holes 603 and the fourth pair of base-traversing fastener holes 607 are distributed on the second lateral section 409 of the base section 4. Moreover, the first pair of base-traversing fastener holes 601 seen in FIG. 1 is concentrically aligned with the second pair of base-traversing fastener holes 603 across the base section 4. Similarly, the third pair of base-traversing fastener holes 605 seen in FIG. 1 is concentrically aligned with the fourth pair of base-traversing fastener holes 607 across the base section 4.

As seen in FIG. 1, the fourth pair of base-traversing fastener holes 607 traverses the second lateral surface 409 and is aligned with the second pair of tower-receiving slots 503. Thus, in a different embodiment, when the second tower section 103 is mounted to the second slot 507 of the second pair of tower-receiving slots 503, the second pair of fasteners 71, also seen in FIG. 1, may be inserted through the fourth pair of base-traversing fastener holes 607 and into the second pair of tower-traversing holes 303 to secure the second tower section 103 with the base section 4.

Figure 2A:
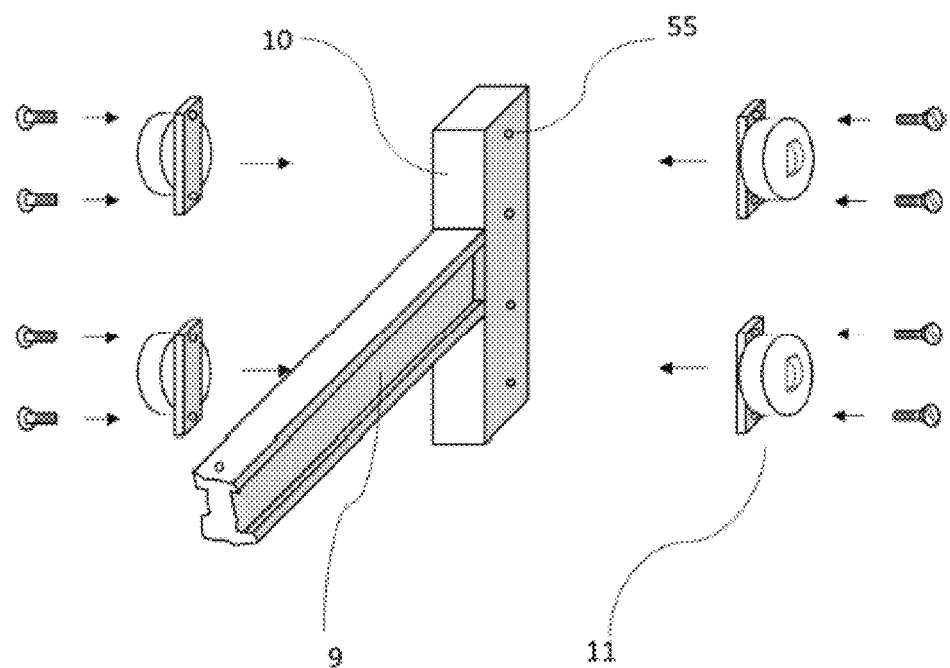
FIG. 2A is a perspective exploded view of the loading beam and a sliding mechanism, wherein the sliding mechanism is used to position the loading beam at different heights along the standing guide tower.
Figure 3A:
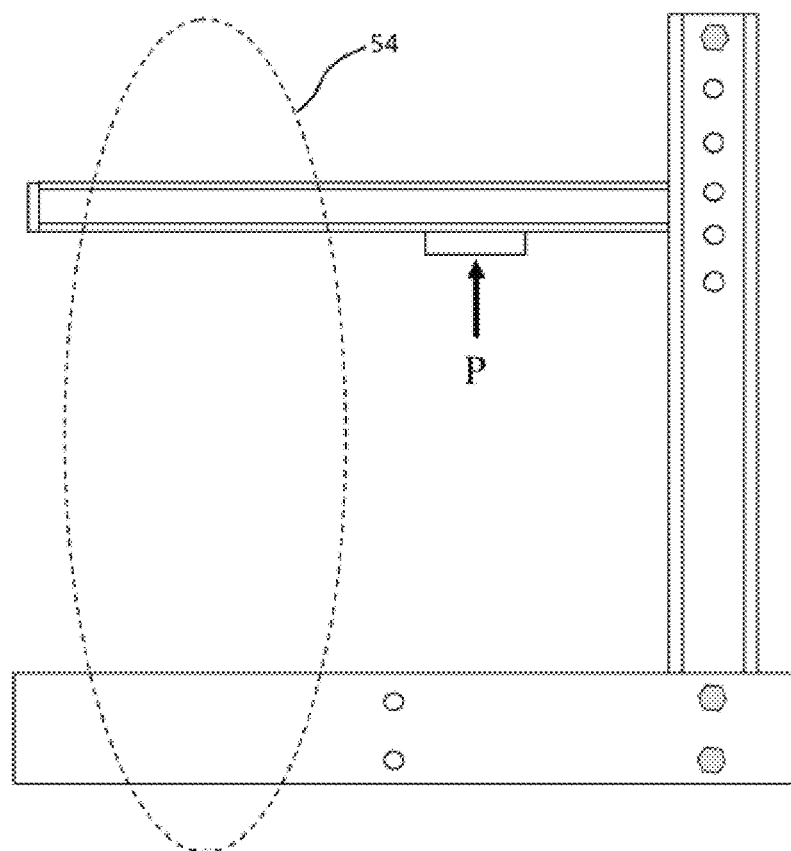
FIG. 3A is a side view of the loading frame described in the present disclosure, wherein the loading beam is in a forward configuration to perform a series of fiber reinforced polymer (FRP)-concrete bond tests.
Figure 3B:
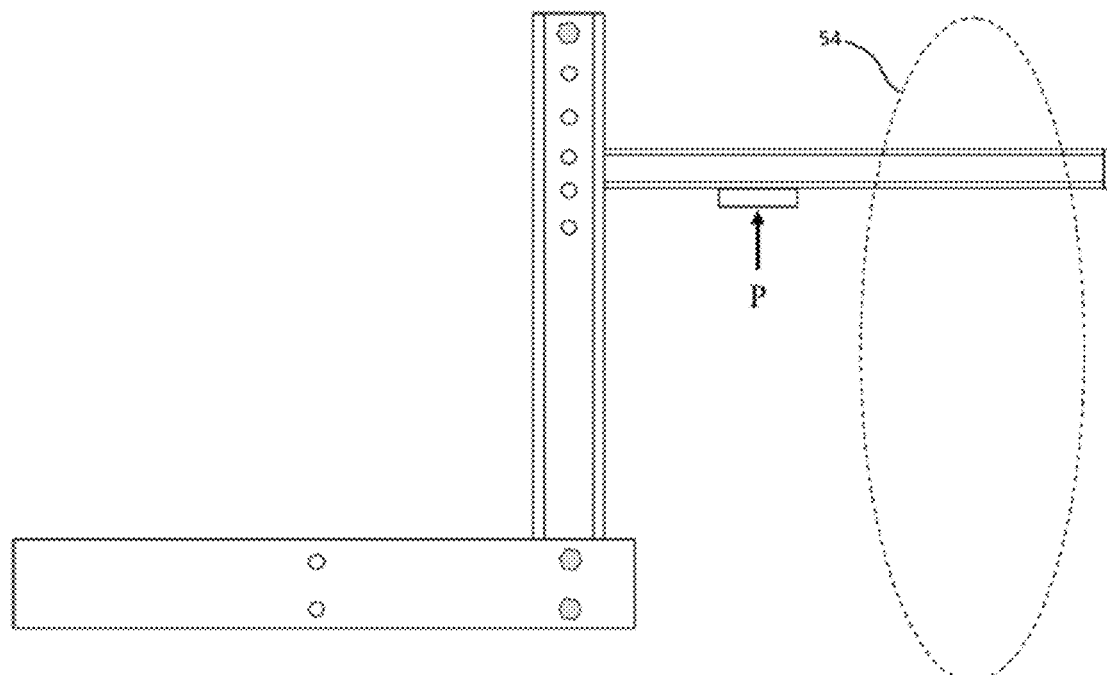
FIG. 3B is a side view of the loading frame described in the present disclosure, wherein the loading beam is in a reverse configuration to perform the series of FRP-concrete bond tests.

The loading beam 9, seen in FIG. 1 and FIGS. 7A-9B, is used to apply a load during each of the series of FRP-concrete bond tests. In a preferred embodiment, as seen in FIG. 1 and FIG. 2A, the loading beam 9 has an I-shaped cross section. As seen in FIG. 2A, the loading beam 9 comprises a sliding end 10 and a free end 100, wherein a distance from the sliding end 10 to the free end 100 determines a length of the loading beam 9. Preferably, as illustrated in FIG. 3A, a length of the base section 4 is substantially similar to a length of the loading beam 9. To allow the use of mobile loading systems such as hydraulic jacks and to reduce secondary forces and reactions during a load application process, as seen in FIG. 1, the sliding end 10 is slidably positioned into the channel 109 configured by the first tower section 101 and the second tower section 103 with a sliding mechanism 11 that may vary in different embodiments. Moreover, as illustrated in FIG. 1, by positioning the sliding end 10 in the channel 109 configured by the first tower section 101 and the second tower section 103, a probability of the loading beam 9 rotating upon load application is reduced. A height from a top surface 401 of the base section 4 to the loading beam 9 may be adjusted by moving the sliding end 10 along a height of the first tower section 101 and the second tower section 103. As seen in FIG. 2A, the sliding end 10 is T-shaped to be positioned within the channel 109 in between the first tower section 101 and the second tower section 103 such that a load applying portion 54 of the loading beam 9 extends out from the standing guide tower 1 shown in FIG. 1. Thus, as seen in FIG. 3A and FIG. 3B, when the sliding end 10 is positioned within the channel 109, the free end 100 extends perpendicular to the standing guide tower 1 and parallel to the base section 4. In further reference to FIG. 3A, when the sliding end 10 is positioned within the channel 109, the loading beam 9 may be in a forward configuration where the loading beam 9 and the base section 4 are oriented in the same direction. In a different embodiment, as seen in FIG. 3B, the loading beam 9 may be in a reverse configuration where the loading beam 9 and the base section 4 are oriented in opposite directions.

Figure 2B:
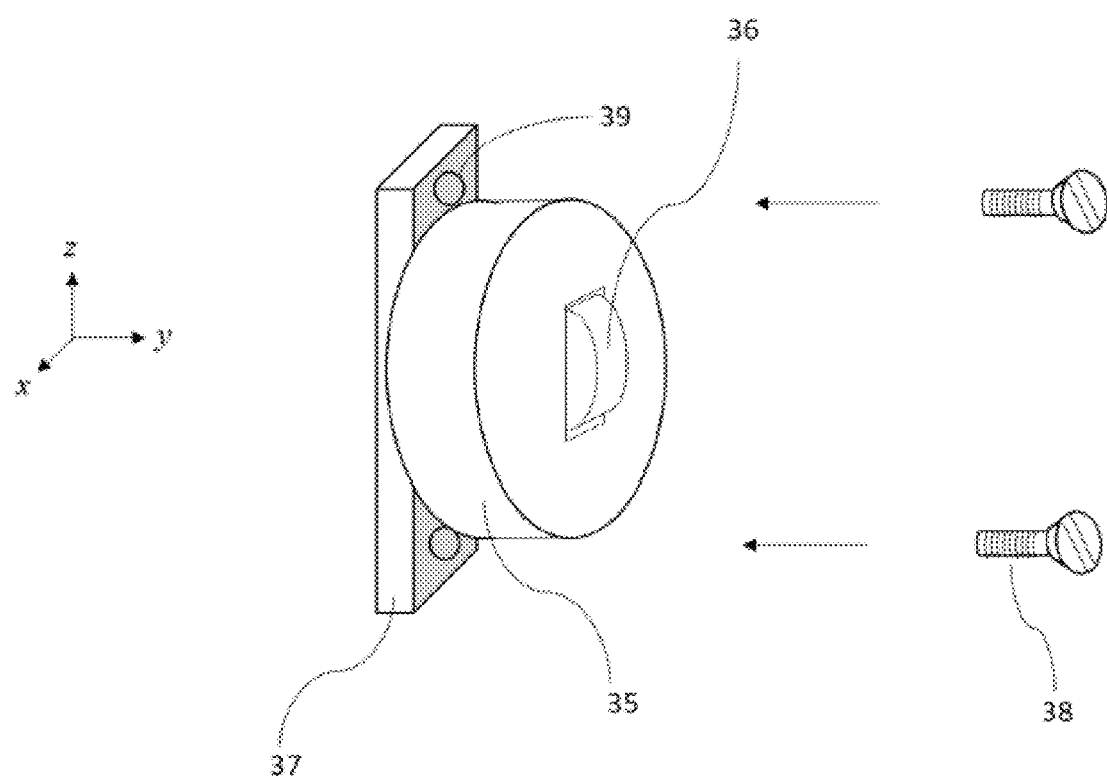
FIG. 2B is a detailed perspective view of an axial sliding wheel and a radial sliding wheel, wherein the radial sliding wheel is perpendicularly and rotatably positioned into a structural body of the axial sliding wheel.

In a preferred embodiment, as seen in FIG. 2A and FIG. 2B, the sliding mechanism 11 used to move the sliding end 10 along the channel 109 comprises a first pair of axial sliding wheels 351, a second pair of axial sliding wheels 353, a first pair of radial sliding wheels 355, and a second pair of radial sliding wheels 357. Preferably, for accurate results and user convenience, the first pair of axial sliding wheels 351, the second pair of axial sliding wheels 353, the first pair of radial sliding wheels 355, and the second pair of radial sliding wheels 357 shown in FIG. 2A may be lubricated to improve sliding capabilities.

The type of lubricant used in the sliding mechanism 11, shown in FIG. 1 and FIG. 2A, may be, but is not limited to a dry polytetrafluoroethylene (PTFE) lubricant, a synthetic grease, a silicone lubricant spray, a marine grease, a rust-penetrating oil, and a white lithium grease. If dry PTFE is used, a thin film of PTFE is deposited onto the first pair of axial sliding wheels 351, the second pair of axial sliding wheels 353, the first pair of radial sliding wheels 355, and the second pair of radial sliding wheels 357 shown in FIG. 2A such that dust accumulation may be reduced. Synthetic grease may improve the performance of the sliding mechanism 11 shown in FIG. 1 and FIG. 2A at high temperatures. The silicone lubricant spray may repel water from sliding components. Marine grease is generally used to lubricate high-load components. Furthermore, marine grease may be used to reduce rust. Rust-penetrating oil may be used to remove rust buildup in sliding components. White lithium grease may be used to lubricate sliding components positioned within a restricted space.

As seen in FIG. 2A, the first pair of radial sliding wheels 355 is rotatably engaged with the first pair of axial sliding wheels 351 to slide along an internal surface 102 of the first tower section 101 shown in FIG. 1, which has a C-shaped cross section and provides a groove for the first pair of radial sliding wheels 355 and the first pair of axial sliding wheels 351 to move along the first tower section 101. In particular, a radial sliding wheel of the first pair of radial sliding wheels 355 is perpendicularly and rotatably positioned into a structural body 360 of an axial sliding wheel of the first pair of axial sliding wheels 351. As illustrated in FIG. 1, the internal surface 102 of the first tower section 101, which is C-shaped, and the engagement between the axial sliding wheel and the radial sliding wheel allows the first pair of axial sliding wheels 351 to move along two opposing portions of the internal surface 102, and the first pair of radial sliding wheels 355 to move along an intermediate portion of the internal surface 102. More specifically, by being tightly pressed against the internal surface 102 of the first tower section 101, the channel 109 configured in between the first tower section 101 and the second tower section 103 shown in FIG. 1 remains unobstructed. To move the sliding end 10 along the internal surface 102 of the first tower section 101 and thereby move the loading beam 9 to different heights, the first pair of axial sliding wheels 351 and the first pair of radial sliding wheels 355 are attached to a first lateral surface 111 of the loading beam 9 with a wheel-holding plate 37 as seen in FIG. 2A. In a preferred embodiment, referring to FIG. 2A, the wheel-holding plate 37 and a set of wheel-holding screws 38 are used to attach each of the first pair of axial sliding wheels 351 to the first lateral surface 111, wherein the set of wheel-holding screws 38 presses an axial sliding wheel against the wheel-holding plate 37 and the first lateral surface 111 of the loading beam 9. As seen in FIG. 2A, the set of wheel-holding screws 38 is positioned through a first pair of screw-receiving slots 39, which traverses the wheel holding plate 37, and a second pair of screw-receiving slots 55 which traverses the first lateral surface 111.

As seen in FIG. 2A and FIG. 2B, the second pair of radial sliding wheels 357 is rotatably engaged with the second pair of axial sliding wheels 353 to slide along an internal surface 104 of the second tower section 103, shown in FIG. 1, which has a C-shaped cross section and provides a groove for the second pair of radial sliding wheels 357 and the second pair of axial sliding wheels 353. In further reference to FIG. 2A and FIG. 2B, a radial sliding wheel of the second pair of radial sliding wheels 357 is perpendicularly and rotatably positioned into a structural body 360 of an axial sliding wheel of the second pair of axial sliding wheels 353. The internal surface 104 of the second tower section 103, which is C-shaped as shown in FIG. 1, and the engagement between the axial sliding wheel and the radial sliding wheel allows the second pair of axial sliding wheels 353 to move along two opposing portions of the internal surface 104 of the second tower section 103. Furthermore, the internal surface 104 of the second tower section 103, which is C-shaped as shown in FIG. 1, allows the second pair of radial sliding wheels 357 to move along an intermediate portion of the internal surface 104. More specifically, by being tightly pressed against the internal surface 104 of the second tower section 103, the channel 109 shown in FIG. 1 remains unobstructed. In reference to FIG. 1 and FIG. 2A, to move the sliding end 10 along the internal surface 104 of the second tower section 103 and thereby move the loading beam 9 to different heights, the second pair of axial sliding wheels 353 and the second pair of radial sliding wheels 357 are attached to a second lateral surface 113 of the loading beam 9. In a preferred embodiment, as seen in FIG. 2A and FIG. 2B, a wheel-holding plate 37 and a set of wheel-holding screws 38 are used to attach each of the second pair of axial sliding wheels 353 to the second lateral surface 113, wherein the set of wheel-holding screws 38 presses an axial sliding wheel against the wheel-holding plate 37 and the second lateral surface 113 of the loading beam 9. In particular, as illustrated in FIG. 2A, the set of wheel-holding screws 38 is positioned through a first pair of screw-receiving slots 39, which traverses the wheel holding plate 37, and into a second pair of screw-receiving slots 55 which traverses the second lateral surface 113.

Figure 14A:
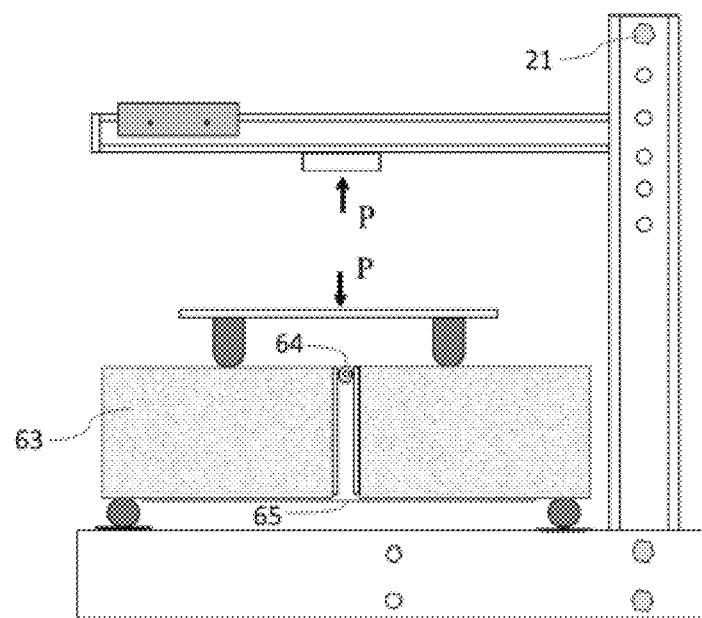
FIG. 14A is a side view of the loading frame described in the present disclosure being used for a beam-bending type test, wherein a load-spreading device is used to distribute a load.
Figure 15A:
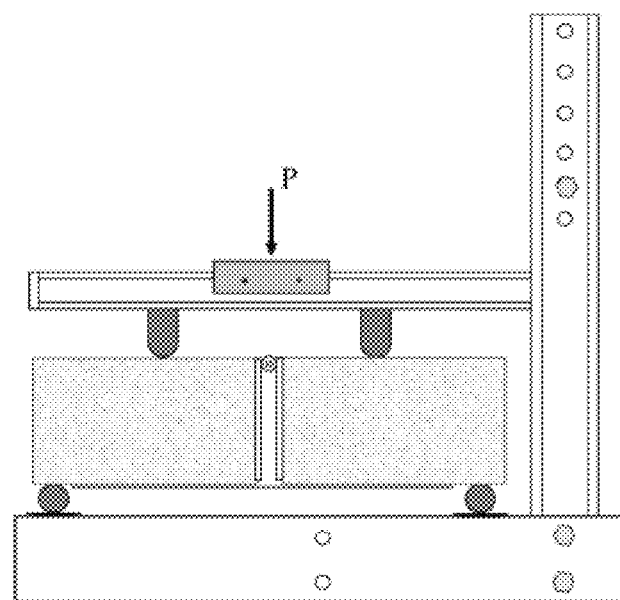
FIG. 15A is a side view of the loading frame described in the present disclosure being used for a beam-bending type test, wherein a load is applied to a loading beam of the loading frame.

As seen in FIG. 14A and FIG. 15A, a test from the series of FRP-concrete bond tests may be performed at different heights by sliding the loading beam 9 along the standing guide tower 1. To provide varying heights for the series of FRP-concrete bond tests, as seen in FIG. 1, FIG. 3A, and FIG. 3B, the standing guide tower 1 comprises a plurality of height-adjusting slots 2 which traverses the first tower section 101 and a second tower section 103 adjacent a top end 107 of the standing guide tower 1. Preferably, as seen in FIG. 1, FIG. 3A, and FIG. 3B, each of the plurality of height-adjusting slots 2 is equidistantly positioned along the first tower section 101 and the second tower section 103. Based on the height required by a FRP-concrete bond test, the loading beam 9 is secured at a preferred slot from the plurality of height-adjusting slots 2.

As seen in FIG. 1, FIG. 3A, and FIG. 3B, to prevent the loading beam 9 from sliding out of the channel 109 from the top end 107 of the standing guide tower 1, a stopping pin 21 is preferably inserted into a slot of the plurality of height-adjusting slots 2 adjacent the top end 107. In a preferred embodiment, as seen in FIG. 1, the stopping pin 21 is secured in the first slot using a pin-fastening nut 22 and a pin-fastening washer 23.

The load applying portion 54, shown in FIG. 3A and FIG. 3B, on the loading beam 9 may differ according to the FRP-concrete bond test from the series of FRP-concrete bond tests. Therefore, as seen in FIG. 1 and FIGS. 7A-7C, to apply the load at a preferred point along a length of the loading beam 9, the loading beam 9 comprises a plurality of positioning slots 12, wherein the plurality of positioning slots 12 is equidistantly distributed along the length of the loading beam 9 in between the free end 100 and the sliding end 10. Preferably, as seen in FIG. 1 and FIGS. 7A-7C, the plurality of positioning slots traverses into a top surface 115 of the loading beam 9.

Figure 8A:
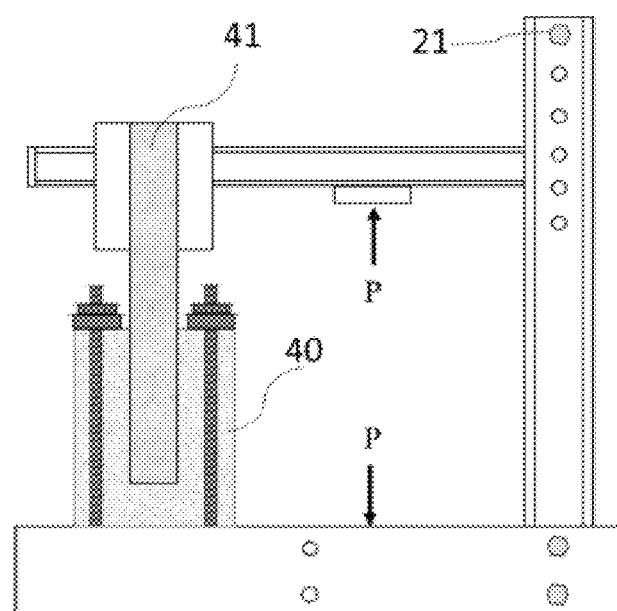
FIG. 8A is a side view of the loading frame described in the present disclosure being used for a double-shear test, wherein the positioning device and the hollow cylinder from a prior art are used to position a FRP test strip around the loading beam.
Figure 8B:
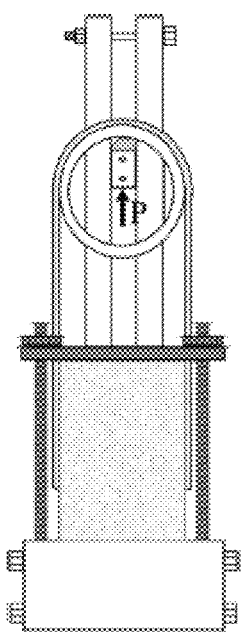
FIG. 8B is a front view of the loading frame described in the present disclosure being used for the double-shear test, wherein the positioning device and the hollow cylinder are used to position the FRP test strip around the loading beam.

To engage with a test apparatus used in a FRP-concrete bond test, the loading frame described in the present disclosure further comprises a coupling device 14 as seen in FIG. 1. As seen in FIG. 8B and FIG. 9B, the coupling device 14 may be used as an intermediate device that connects the loading beam 9 to a testing setup. As seen in FIG. 1, FIG. 7A, and FIG. 7B, the coupling device 14 is positioned into a selected slot from the plurality of positioning slots 12 with an attachment mechanism that may be, but is not limited to, a positioning screw 20 which is inserted into a positioning screw-receiving hole 18 that traverses through a top surface of the coupling device 14. Referring to FIG. 7A and FIG. 7B, by concentrically aligning the positioning screw-receiving hole 18 with the selected slot on the loading beam 9, and inserting the positioning screw 20 through the positioning screw-receiving hole 18 into the selected slot, the coupling device 14 may be positioned along the loading beam 9.

As seen in FIG. 1, a stopper plate 15 may be used to prevent the coupling device 14 from sliding beyond the free end 100. In further reference to FIG. 1, a pair of plate fastening screws 17 may be positioned through a first pair of plate-fastening screw receiving holes 16 that traverses the stopper plate 15 and into a second pair of plate-fastening screw receiving holes 166 that traverses the loading beam 9 at the free end 100. Preferably, as seen in FIG. 8B and FIG. 9B, the stopper plate 15 is rectangular in shape such that a perimeter of the stopper plate 15 overlaps the I-shaped cross section of the loading beam 9.

In one embodiment, as seen in FIG. 1, FIG. 16, FIG. 19B, and FIG. 21B, the coupling device 14 may be a rectangular block 140 comprising a beam-receiving groove 59. The top surface 115 of the loading beam 9 is positioned into the beam-receiving groove 59 such that the coupling device 14 is engaged to the loading beam 9.

As seen in FIG. 7A and FIG. 8B, in one embodiment, the coupling device 14 comprises a positioning device 56 and a hollow cylinder 57. As illustrated in FIG. 7A, the positioning device 56 is positioned along the top surface 115 of the loading beam 9 and engaged to a selected slot of the plurality of positioning slots 12. Preferably, as seen in FIG. 8B, the positioning device 56 is semi-cylindrical in shape and has a diameter equal to a width of the top surface 115 of the loading beam 9. Further referring to FIG. 8B, the hollow cylinder 57 is detachably attached to the positioning device 56 such that the hollow cylinder 57 perimetrically sleeves the positioning device 56. More specifically, a curvature of the positioning device 56 is matched by the hollow cylinder 57 such that a FRP test strip 65 may be positioned along an external surface 577 of the hollow cylinder 57 creating an arc as shown in FIG. 8B.

As seen in FIG. 7B and FIG. 9B, in one embodiment, the coupling device 14 is a semi-cylindrical device 58 comprising a beam-receiving groove 59. The top surface 115 of the loading beam 9 is positioned into the beam-receiving groove 59 of the semi-cylindrical device 58 to engage the semi-cylindrical device 58 with the loading beam 9. As shown in FIG. 7B, to secure the semi-cylindrical device 58 along the loading beam 9, the positioning screw 20 is positioned through the positioning screw-receiving hole 18, which traverses the semi-cylindrical device 58, and positioned into a selected slot of the plurality of positioning slots 12. As shown in FIG. 9B, a curvature of the semi-cylindrical device 58 allows a FRP test strip 65 to be positioned along an external surface 588 of the semi-cylindrical device 58 creating an arc.

Figure 17A:
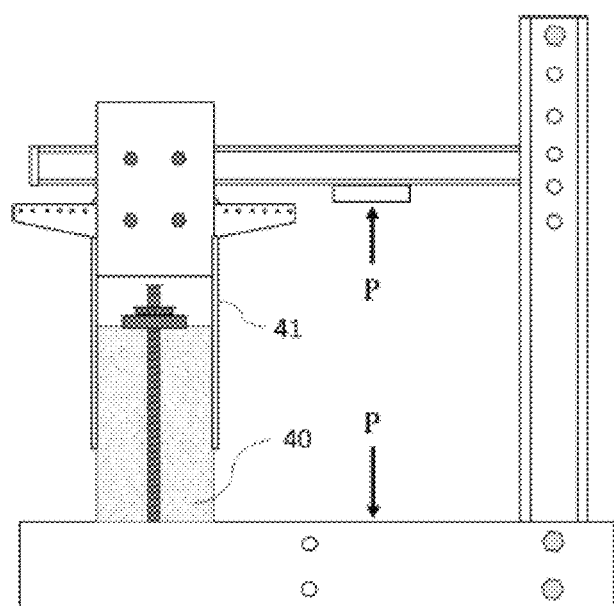
FIG. 17A is a side view of the loading frame described in the present disclosure being used for a double-shear test, wherein the debonding test apparatus is used to perform the double-shear test.
Figure 17B:
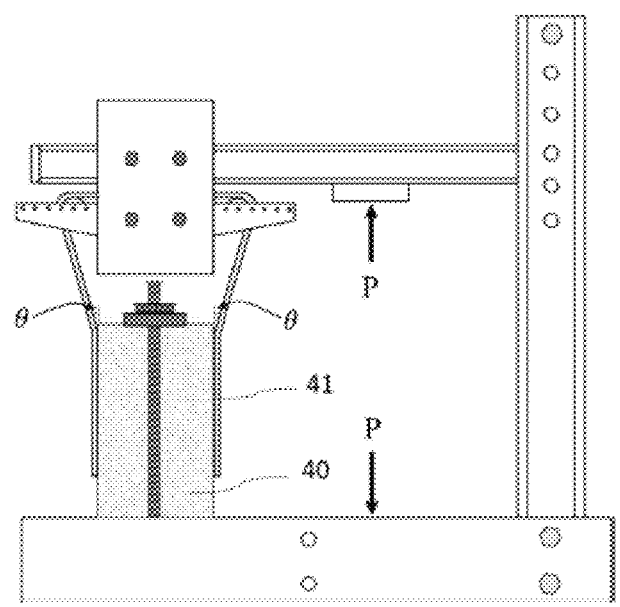
FIG. 17B is a side view of the loading frame described in the present disclosure being used for a mixed-mode test, wherein the debonding test apparatus is used to perform the mixed-mode test, wherein shearing and peeling are tested in the mixed-mode test.
Figure 18:
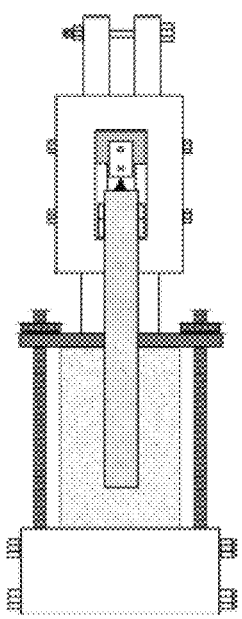
FIG. 18 is a side view of the loading frame described in the present disclosure being used for the double-shear test and/or the mixed-mode test, wherein the debonding test apparatus is used to perform the double-shear test and/or the mixed-mode test.

As seen in FIG. 1 and FIGS. 7A-7C, to hold the concrete block 40 against the top surface 401 of the base section 4, wherein the concrete block 40 is used in each of the series of FRP-concrete bond tests, the loading frame described in the present disclosure comprises at least a pair of rod-receiving holes 8 which traverses into the top surface 401 of the base section 4 adjacent the second end 405 of the base section 4. As seen in FIGS. 7A-7C, a second pair of rod-receiving holes 83, a third pair of rod-receiving holes 85, and a fourth pair of rod-receiving holes 87 may also traverse into the top surface 401 of the base section 4 to provide additional engagement points for the concrete block. In further reference to FIGS. 7A-7C, preferably, the first pair of rod-receiving holes 81, the second pair of rod-receiving holes 83, the third pair of rod-receiving holes 85, and the fourth pair of rod-receiving holes 87 are equidistantly positioned along the top surface 401 of the base section 4. To hold the concrete block against the top surface 401 of the base section 4, as shown in FIG. 1, a pair of rods 24 and a holding plate 25 are preferably used with the pair of rod-receiving holes 8. More specifically, as shown in FIG. 1, a first terminal end 245 of the pair of rods 24 is positioned into the pair of rod-receiving holes 8 such that the concrete block may be positioned in between each rod of the pair of rods 24. As shown in FIGS. 17A-18, the holding plate 25 is pressed against a top surface 445 of the concrete block 40 such that the concrete block 40 is held in between the holding plate 25 and the top surface 401 of the base section 4. As seen in FIG. 18, a second terminal end 247 of the pair of rods 8 is positioned through the holding plate 25 such that the holding plate 25 is engaged with the base section 4. In further reference to FIG. 18, preferably, a pair of rod-securing nuts 26 is used to establish a physical connection between the holding plate 25 and the pair of rods 8 at the second terminal end 247.

Figure 13A:
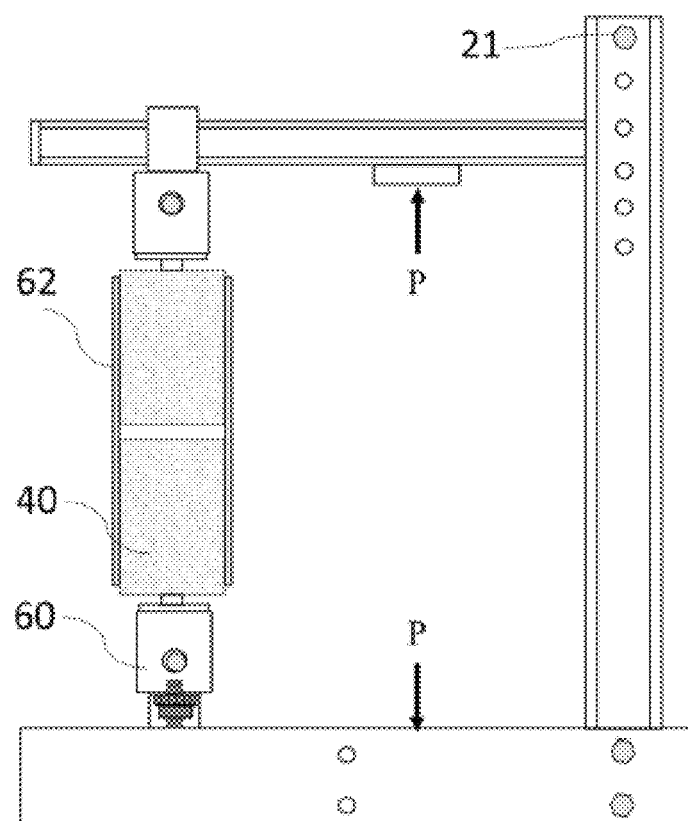
FIG. 13A is a side view of the loading frame described in the present disclosure being used for a double-shear test, wherein the first clamping device and a second clamping device from a prior art are used to perform the double-shear test.
Figure 13B:
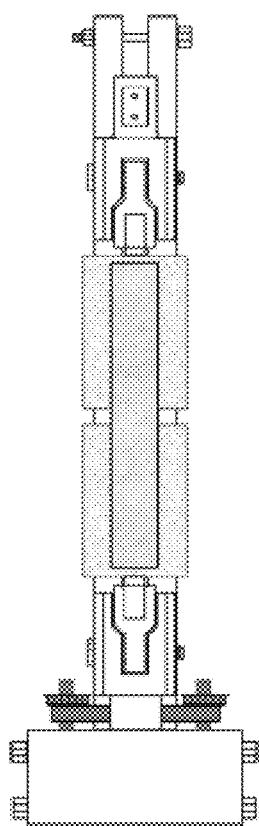
FIG. 13B is a front view of the loading frame described in the present disclosure being used for a double-shear test, wherein the first clamping device and the second clamping device from a prior art are used to perform the double-shear test.

As seen in FIG. 7C, FIG. 13A, and FIG. 13B, in a different embodiment, the loading frame described in the present disclosure comprises a first clamping device 600 and a second clamping device 601. In reference to FIG. 13A and FIG. 13B, the first clamping device 600 is attached to a first concrete block 411 and the second clamping device 601 is attached to a second concrete block 413, wherein the first concrete block 411 and the second concrete block 413 are attached to each other through a pair of FRP strips 651. As seen in FIG. 7C, the first clamping device 600 and the second clamping device 601 each comprises an attachment protrusion 61 that is configured to receive an external component. In further reference to FIG. 7C, the free end 100 of the loading beam 9 may be inserted into the attachment protrusion 61 of the first clamping device 600 such that the first clamping device 601 is engaged to the loading beam 9 at a selected slot from the plurality of positioning slots 12 on the loading beam 9.

As seen in FIG. 7C, FIG. 13A, and FIG. 13B, the second clamping device 601 is attached to the base section 4 with a holding plate 25 and a pair of clamp-securing rods 62. When attaching the second clamping device 601, as seen in FIG. 7C, a first end 622 of the pair of clamp-securing rods 62 is inserted into the pair of rod-receiving holes 8 positioned adjacent the second end 405 of the base section 4. As seen in FIG. 13A and FIG. 13B, the holding plate 25 is inserted through the attachment protrusion 61 of the second clamping device 601 and subsequently attached to a second end 623 of the pair of clamp-securing rods 62. As illustrated in FIG. 13A, when a double-shear test is performed, the attachment between the first clamping device 600 and the loading beam 9 allows an upward force, $P_1$, to be applied on the pair of FRP strips 651. In further reference to FIG. 13A, the attachment between the base section 4 and the second clamping device 601 allows a downward force, $P_2$, to be applied on the pair of FRP strips 651.

Figure 16:
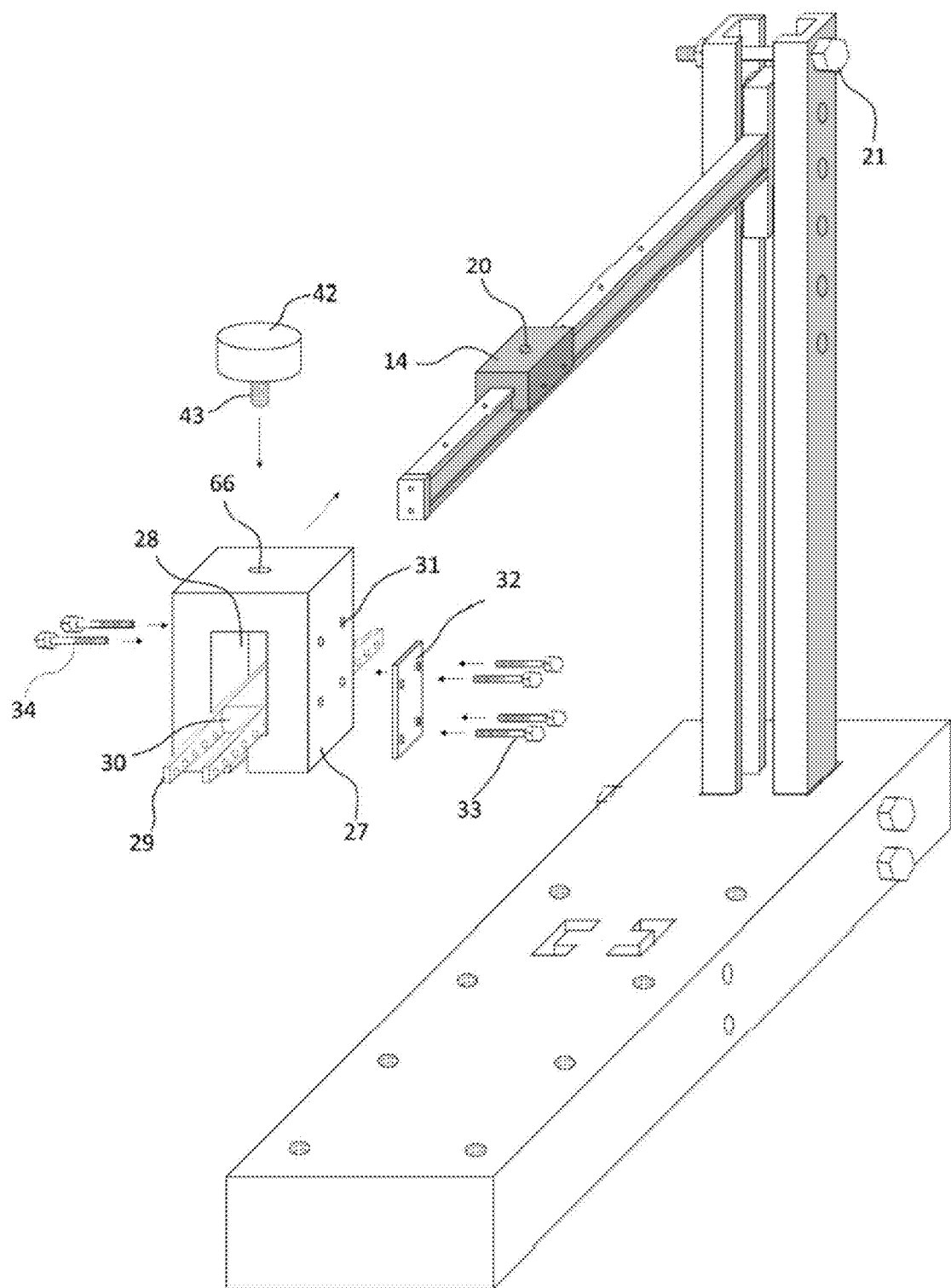
FIG. 16 is a perspective view of the loading frame, wherein the standing guide tower, the base section, the loading beam, and an exploded view of a debonding test apparatus are illustrated.

To perform the series of FRP-concrete bond tests, as seen in FIG. 16, the loading frame described in the present disclosure further comprises a debonding test apparatus 270, which is a convertible testing device, is removably attached to the loading beam 9. As seen in FIGS. 17A-19B and FIGS. 21A-25, the debonding test apparatus 270 may be used to perform double-shear tests, single-shear tests, and direct tension pull-off tests. In a different embodiment, the debonding test apparatus 270, shown in of FIG. 16, may also be configured to perform beam-bending type tests. Therefore, by utilizing the debonding test apparatus 270 of FIG. 16, the loading frame described in the present disclosure may be configured to a convertible FRP-concrete bond testing setup, an adaptable testing setup capable of being used with existing FRP-concrete bond tests, a mobile testing setup, and a testing setup which improves efficiency by reducing secondary forces during load application.

Figure 21A:
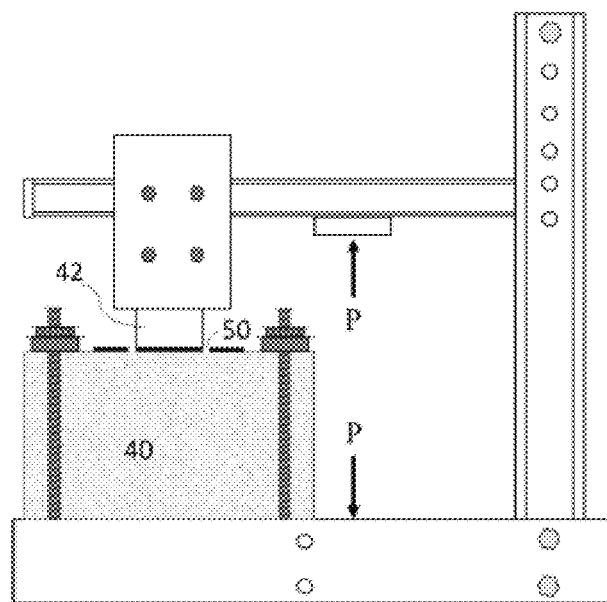
FIG. 21A is a side view of the debonding test apparatus being used for the direct tension pull-off test, wherein a tension pull-off disk of the debonding test apparatus is attached to the FRP sheet layered on the concrete block.
Figure 21B:
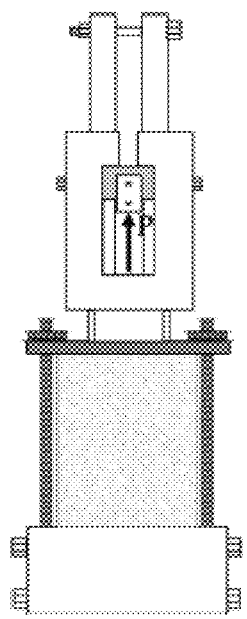
FIG. 21B is a front view of the debonding test apparatus being used for the direct tension pull-off test, wherein the tension pull-off disk of the debonding test apparatus is attached to an FRP sheet layered on a concrete block.

As illustrated in FIG. 16, the debonding test apparatus 270 comprises a structural block 27 and an adjustable hanger 29, wherein the adjustable hanger 29, which may be used to apply a pulling force on a FRP test strip 65 at varying angles, is positioned into a receiving slot 28 formed within the structural block 27. As seen in FIG. 16, a bottom end 283 of the receiving slot 28 is at a bottom surface 274 of the structural block 27. In further reference to FIG. 16, the receiving slot 28 extends from the bottom end 283 to a top end 281, wherein the top end 281 is positioned adjacent a top surface 272 of the structural block 27. Preferably, as shown in FIG. 16, the adjustable hanger 29 is positioned in the receiving slot 28 adjacent the bottom end 283. In a preferred embodiment, the receiving slot 28 is rectangular in shape as seen in FIG. 16 and FIG. 18. Therefore, as illustrated in FIG. 16, the coupling device 14 used to attach the debonding test apparatus 270 to the loading beam 9 is a rectangular block 140 comprising a beam-receiving groove 59, wherein the coupling device 14 is held at a preferred slot from the plurality of positioning slots 12 on the loading beam 9. As shown in FIG. 18, FIG. 19B, and FIG. 21B, the loading beam 9 and the coupling device 14 are slidably positioned into the receiving slot 28.

To perform the series of FRP-concrete bond tests, the debonding test apparatus 270 further comprises an attachment plate 32 as seen in FIG. 16, wherein the attachment plate 32 is detachably attached to a lateral surface 271 of the structural block 27.

As shown in FIG. 16, to perform the series of FRP-concrete bond tests, the debonding test apparatus 270 further comprises a tension pull-off disk 42 and a top-receiving threaded channel 66 that centrally traverses into the top surface 272 of the structural block 27. The tension pull-off disk 42 comprises a threaded protrusion 43 that extends outwards from a structural body 420 of the tension pull-off disk 42 as seen in FIG. 16. Therefore, as illustrated in FIG. 16, the tension pull-off disk 42 may be attached to the structural block 27 by threadably engaging the threaded protrusion 43 with a plurality of threads 433 that is internally distributed within the top-receiving threaded channel 66.

Figure 4:
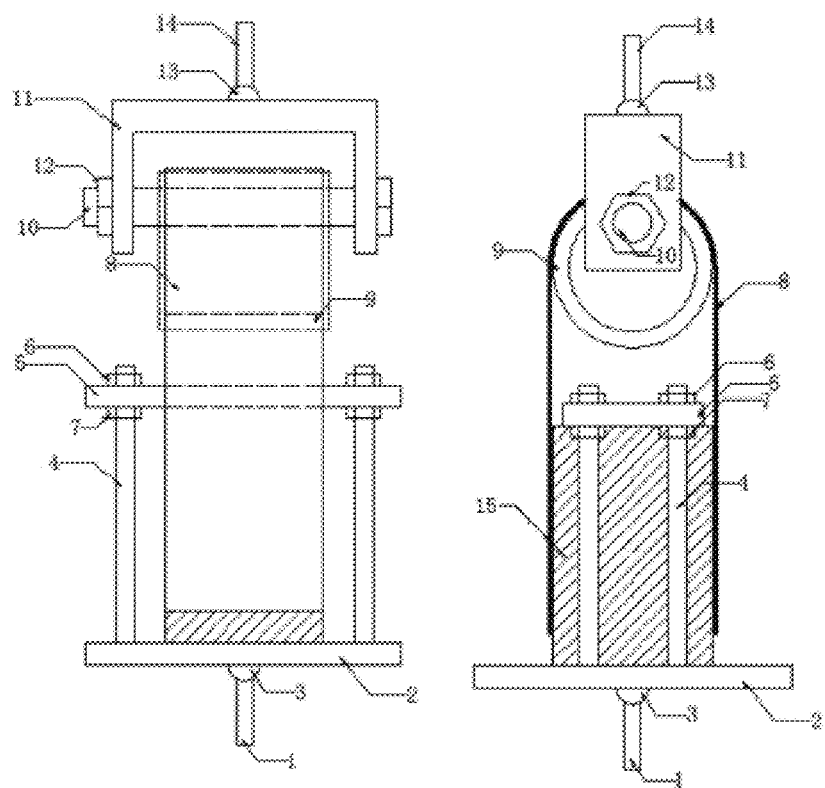
FIG. 4 is an illustration of a testing setup used in a prior art to perform a double-shear test.
Figure 9A:
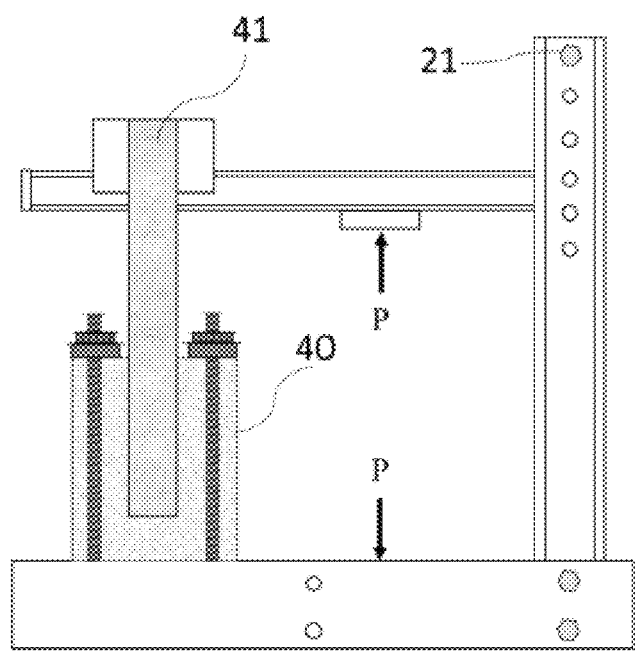
FIG. 9A is a side view of the loading frame described in the present disclosure being used for a double-shear test, wherein the semi-cylindrical device is used to position the FRP test strip around the loading beam.
Figure 9B:
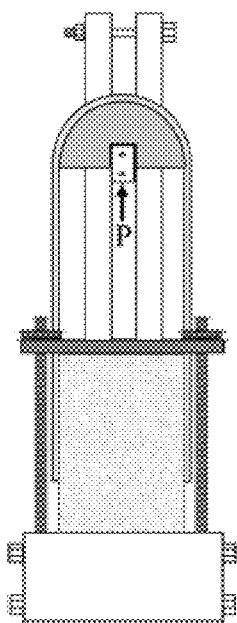
FIG. 9B is a front view of the loading frame described in the present disclosure being used for a double-shear test, wherein the semi-cylindrical device is used to position the FRP test strip around the loading beam.
Figure 10A:
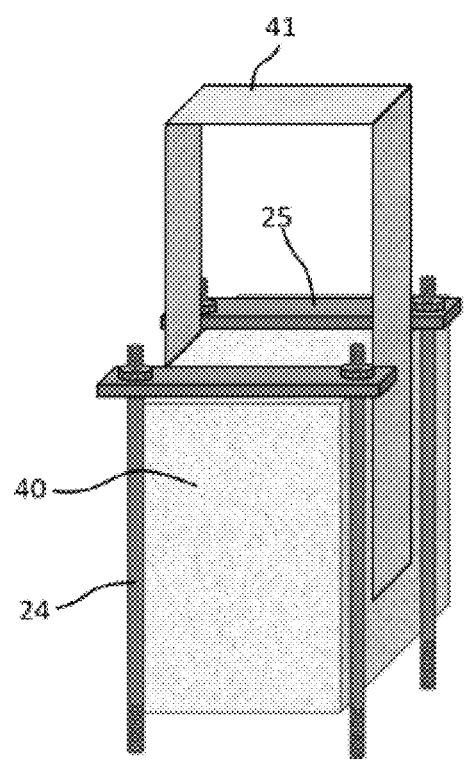
FIG. 10A is a perspective view of an assembly that includes a FRP test strip, a concrete block, a first holding plate, a second holding plate, a first pair of rods, and a second pair of rods, wherein the FRP test strip and the concrete block are used with the loading frame of the present disclosure to perform a double-shear test, wherein the FRP test strip is positioned in between the first holding plate and the second holding plate, wherein the first holding plate, the second holding plate, the first pair of rods, and the second pair of rods are used to hold the concrete block against a top surface of the base section.
Figure 10B:
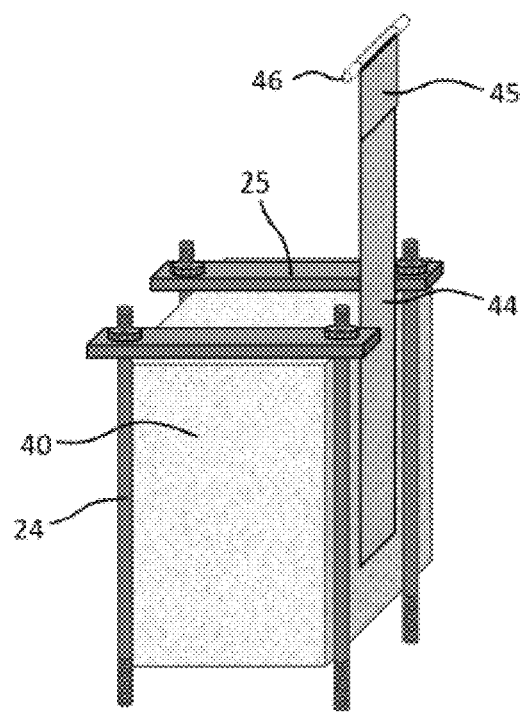
FIG. 10B is a perspective view of an assembly that includes a FRP test strip, a concrete block, a first holding plate, a second holding plate, a first pair of rods, and a second pair of rods, wherein the FRP test strip and the concrete block are used with the loading frame of the present disclosure to perform a single-shear test, wherein the first holding plate, the second holding plate, the first pair of rods, and the second pair of rods are used to hold the concrete block against a top surface of the base section.

As illustrated in FIGS. 8A-9B, the double-shear test for a FRP-concrete bond may also be performed with one concrete block and one FRP test strip, wherein one end of the FRP test strip 65 is attached to a first lateral surface 441 of the concrete block 40 and an opposing end of the FRP strip is attached to a second lateral surface 443 of the concrete block 40 such that the FRP test strip creates a U-shaped loop as seen in FIG. 10A. See "Externally bonded FRP reinforcement dual shear test charger," CN104344989B, incorporated herein by reference in its entirety. As seen in FIG. 4A and FIG. 4B, when only one concrete block is used with one FRP strip in existing testing setups, to perform the double-shear test for the FRP-concrete bond, a hollow cylinder may be used with a load application mechanism.

In comparison, when the loading frame described in the present disclosure is used to perform the double-shear test for a FRP-concrete bond, the positioning device 56 and the hollow cylinder 57 shown in FIG. 7A are used in one embodiment. More specifically, as seen in FIG. 8A and FIG. 8B, the FRP test strip 65 which is connected to the first lateral surface 441 of the concrete block 40 at one end and connected to the second lateral surface 443 of the concrete block 40 at an opposing end is positioned along an external surface 577 of the hollow cylinder 57. As seen in FIG. 8A, to perform the double-shear test for the FRP-concrete bond test, a first load, $P_1$, is applied to a bottom surface 117 of the loading beam 9 and a second load, $P_2$, is applied to the top surface 401 of the base section 4. The first load and the second load are substantially equal to each other and opposite in direction. A loading system that may be, but is not limited to, a hydraulic jack may be used to apply the first load and the second load. The first load and the second load are increased to a shear load, which is the load applied when bond failure occurs in the FRP-concrete bond. Subsequently, the shear load is recorded for the first load and the second load.

Figure 5:
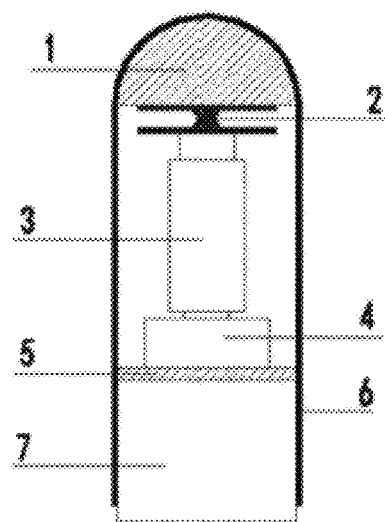
FIG. 5 is an illustration of a mobile hydraulic jack from prior art used to apply a load during the series of FRP-concrete bond tests.

When the FRP test strip 65 is attached to the concrete block 40 illustrated in FIG. 10A, a mobile hydraulic jack or other comparable loading system, as shown in FIG. 5, may be used for load application during the double-shear test. See "Experimental experiment loading device of carbon cloth double shear," CN205593860U, incorporated herein by reference in its entirety. As seen in FIG. 5, with existing testing setups, a semi-circular solid cylinder is generally used to position the FRP test strip during the double-shear test.

In comparison, when the loading frame described in the present disclosure is used to perform the double-shear test for a FRP-concrete bond test, as seen in FIG. 7B, FIG. 9A and FIG. 9B, the semi-cylindrical device 58 comprising the beam-receiving groove 59 may be used during the double-shear test. As illustrated in FIG. 9A, when the semi-cylindrical device 58 is used to perform the double-shear test for the FRP-concrete bond, a first load, $P_1$, is applied to a bottom surface 117 of the loading beam 9 and a second load, $P_2$, is applied to the top surface 401 of the base section 4. The first load and the second load are substantially equal to each other and opposite in direction. The first load and the second load are increased to a shear load, which is the load applied when bond failure occurs in the FRP-concrete bond. Subsequently, the shear load is recorded for the first load and the second load.

Figure 11A:
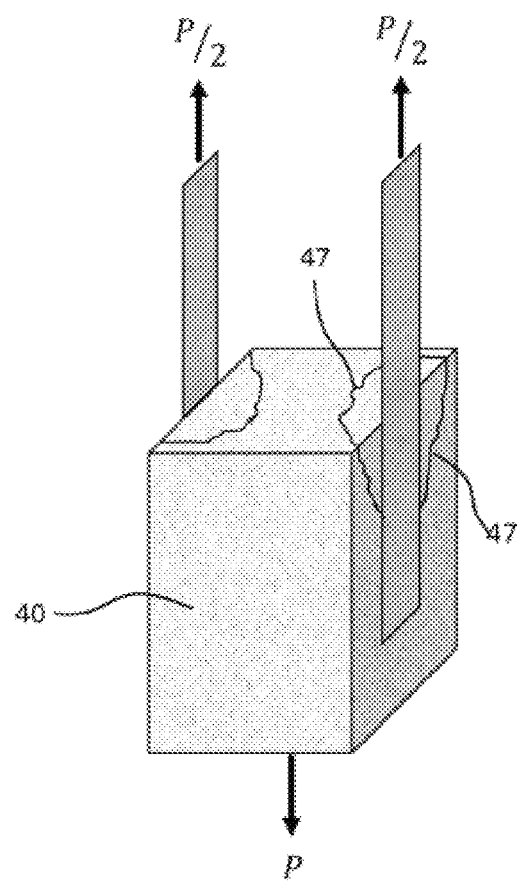
FIG. 11A is an illustration of wedge failure that may occur when the double-shear test is performed using the assembly shown in FIG. 10A.
Figure 11B:
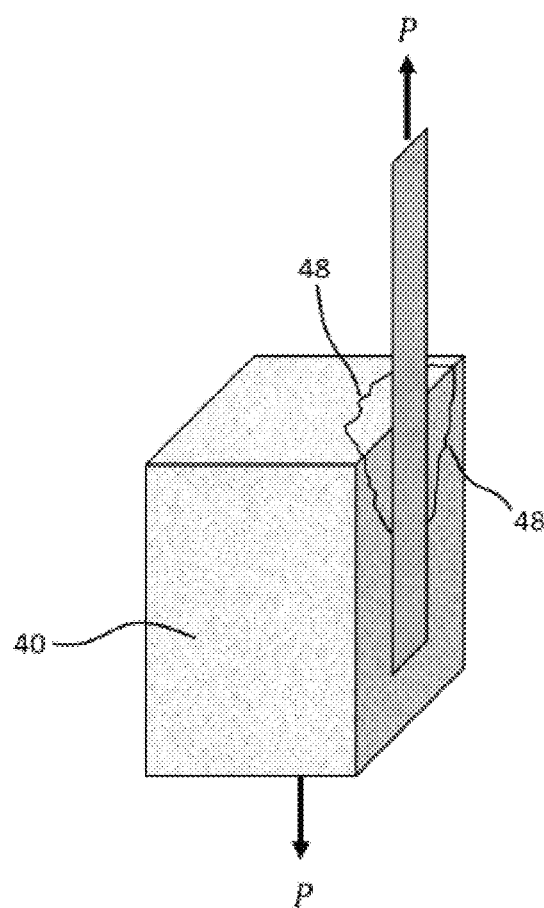
FIG. 11B is an illustration of wedge failure that may occur when the single-shear test is performed using the assembly shown in FIG. 10B.

As seen in FIGS. 8A-9B, the concrete block 40 is held against the top surface 401 of the base section 4 with a first holding plate 251, a second holding plate 253, a first pair of rods 241, and a second pair of rods 243. In one embodiment, a first terminal end 245 of the first pair of rods 241, as seen in FIG. 10A, is positioned into the first pair of rod-receiving holes 81 shown in FIG. 7B. A second terminal end 247 of the first pair of rods 241, as seen in FIG. 10A, is positioned through the first holding plate 251 to hold the concrete block 40 against the top surface 401 of the base section 4 as seen in FIGS. 8A-9B. Moreover, a first terminal end 245 of the second pair of rods 243, shown in FIG. 10A, is positioned into the second pair of rod-receiving holes 83 seen in FIG. 7B. As seen in FIG. 10A, a second terminal end 247 of the second pair of rods 243 is positioned through the second holding plate 253 such that the concrete block 40 may be pressed against the top surface 401 of the base section 4 as seen in FIGS. 8A-9B. The FRP test strip 65 is positioned in between the first holding plate 251 and the second holding plate 253 such that the first holding plate 251, the FRP test strip 65, and the second holding plate 253 are parallel to each other as seen in FIG. 10A. The arrangement of the first holding plate 251 and the second holding plate 253 shown in FIG. 10A, and the loads applied on the FRP test strip 65 may lead to wedge failure as illustrated in FIG. 11A.

Figure 12A:
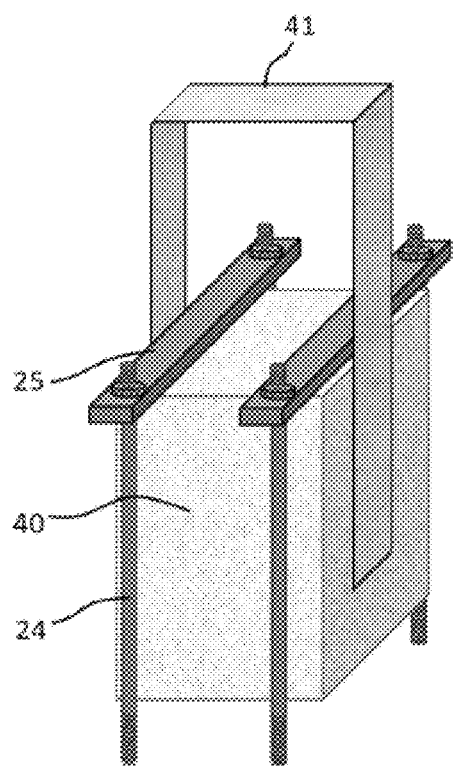
FIG. 12A is a perspective view of an assembly that includes a FRP test strip, a concrete block, a first holding plate, a second holding plate, a first pair of rods, and a second pair of rods in a preferred configuration to reduce a probability of wedge failure during a double-shear test, wherein the first holding plate, the second holding plate, the first pair of rods, and the second pair of rods are used to hold the concrete block against a top surface of the base section.

To reduce the probability of wedge failure, the first terminal end 245 of the first pair of rods 241, seen in FIG. 12A, is positioned into the first pair of rod-receiving holes 81, seen in FIG. 7B, and the first terminal end 245 of the second pair of rods 243, seen in FIG. 12A, is positioned into the second pair of rod-receiving holes 83 of FIG. 7B. However, in place of attaching the first holding plate 251 to the second terminal end 247 of the first pair of rods 241, as shown in FIG. 10A, the first holding plate 251 is positioned through the second terminal end 247 of a rod from the first pair of rods 241 and the second terminal end 247 of a rod from the second pair of rods 243 as seen in FIG. 12A. Similarly, in further reference to FIG. 12A, the second holding plate 253 is positioned through the second terminal end 247 of a rod from the first pair of rods 241, and the second terminal end 247 of a rod from the second pair of rods 243. Thus, as seen in FIG. 12A, the first holding plate 251 and the second holding plate 253 are positioned perpendicular to the FRP test strip 65.

Figure 6A:
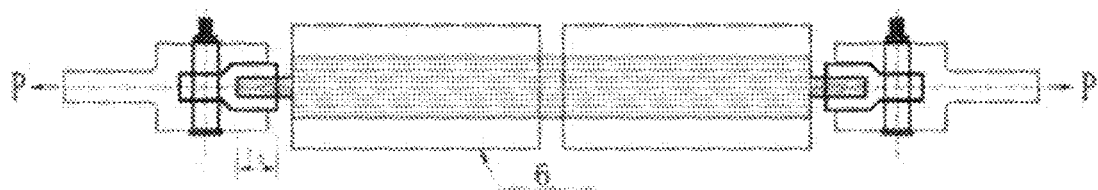
FIG. 6A is an illustration of a testing setup used in a prior art, wherein a pair of concrete blocks and a pair of clamping devices are used to perform a double-shear test.

Generally, in reference to FIG. 6A, when existing testing devices are used to perform the series of FRP-concrete bond tests, a double-shear test for a FRP-concrete bond may be performed with two concrete blocks, wherein the two concrete blocks are attached together with a pair of FRP strips. In particular, a first strip of the pair of FRP strips may be attached to a first lateral surface of the first concrete block at one end and a first lateral surface of a second concrete block at an opposing end. A second strip of the pair of FRP strips may be attached to a second lateral surface of the first concrete block at one end and a second lateral surface of the second concrete block at an opposing end.

As seen in FIG. 6A, the pair of concrete blocks are connected to each other through the pair of FRP test strips while maintaining a gap in between each of the pair of concrete blocks. Further referring to FIG. 6A, to perform the double-shear test in the presence of two concrete blocks using a previously disclosed testing apparatus, a first load and a second load, which are substantially equal and opposite in direction, are applied through a clamping mechanism. The clamping mechanism, shown in FIG. 6B, differs from the conventional method of applying loads directly through axial rebars during double-shear testing. The clamping mechanism allows free rotation of the pair concrete blocks when the first load and the second load are applied and thus, reduces bending/twisting of the concrete blocks that may be detrimental to the results of the double-shear test. Similar to other existing testing devices, when a pair of concrete blocks are used the first load and the second load are applied through a fixed-position loading machine. See "A kind of anti-eccentric loading clamp of double-shear experiment holds device and method," CN107817172A, incorporated herein by reference in its entirety.

Figure 6B:
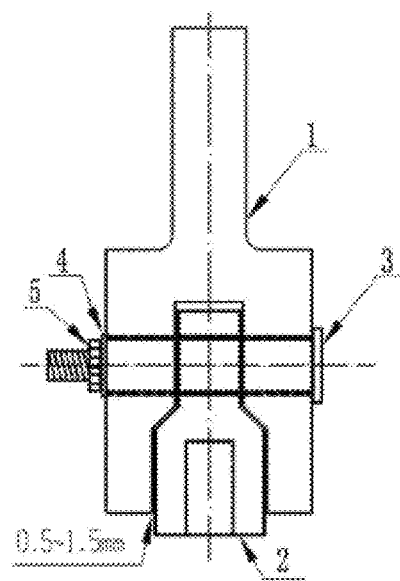
FIG. 6B is a detailed view of a clamping device shown in FIG. 6A, wherein the clamping device is attached to a concrete block to perform the double-shear test.

As seen in FIG. 13A and FIG. 13B, the loading frame described in the present disclosure may be used to perform the double-shear test for a FRP-concrete bond, wherein a first concrete block 411 is attached to a second concrete block 413 with a pair of FRP strips 651. In particular, as seen in FIG. 13A, a first strip 653 of the pair of FRP strips 651 may be attached to a front surface 442 of the first concrete block 411 at one end of the first strip 651, and attached to a front surface 442 of a second concrete block 413 at an opposing end of the first strip 651. A second strip 655 of the pair of FRP strips 651 may be attached to a rear surface 444 of the first concrete block 411 at one end of the second strip 655 and a rear surface 444 of the second concrete block 413 at an opposing end of the second strip 655. As seen in FIG. 13A, the loading frame of the present disclosure may be used to apply a load on the first concrete block 411 and the second concrete block 413 with the first clamping device 600 and the second clamping device 601, shown in FIG. 7C, that are engaged to the first concrete block 411 and the second concrete block 413 respectively. The loading process of FIG. 13A is comparable to the load application process of the existing testing devices as shown in FIG. 6A and FIG. 6B. When the first clamping device 600 and the second clamping device 601 are used for load application purposes, as seen in FIG. 13A, the first clamping device 600, which holds the first concrete block 411, is attached to the loading beam 9 using the attachment protrusion 61 of the first clamping device 600. Further referring to FIG. 13A, the second clamping device 601, which holds the second concrete block 413, is attached to the base section 4 by positioning the holding plate 25 through the attachment protrusion 61 of the second clamping device 601, and connecting the holding plate 25 to the base section 4 with the pair of clamp-securing rods 62. As seen in FIG. 13A and FIG. 13B, to perform the double-shear test for the FRP-concrete bond, a first load, $P_1$, is applied to a bottom surface 117 of the loading beam 9 and a second load, $P_2$, is applied to the top surface 401 of the base section 4. The first load and the second load are substantially equal to each other and opposite in direction. Preferably, referring to FIG. 13A, the first load and the second load are applied using a hydraulic jack which positioned on the base section 4, and in between the standing guide tower 1 and the second clamping device 601. The first load and the second load are increased to a shear load, which is the load applied when bond failure occurs in the FRP-concrete bond. Subsequently, the shear load is recorded for the first load and the second load.

The loading frame described in the present disclosure may be adapted to be used with existing beam-bending testing devices and test setups. Generally, two techniques are used to perform the beam-bending type tests.

In a first technique, two concrete blocks are aligned adjacent to each other, wherein each concrete block is flipped on a positioning surface such that a bottom surface of each concrete block is perpendicular to the positioning surface. Since the concrete blocks are positioned adjacent to each other, a bottom surface of the first concrete block is positioned adjacent the top surface of the second concrete block and the bottom surface of the first concrete block is connected to a top surface of the second concrete block using a hinge. Moreover, a front surface of the first concrete block is connected to a front surface of the second concrete block with an FRP strip. When performing the beam-bending type test, a load is applied at a rear surface of the first concrete block and a rear surface of the second concrete block using a load-spreading device. The load-spreading device distributes the load equally between the first concrete block and the second concrete block. More specifically, the load is applied to the rear surface of the first concrete block at a first loading point. The load is applied to the rear surface of the second concrete block at a second loading point.

In a second technique, a concrete block with a precracked surface may be used, wherein the precracked surface is used to determine a path of propagation of a crack associated with the precracked surface. The FRP strip is attached to the precracked surface and a load is applied to a surface opposite to the precracked surface.

As seen in FIGS. 14A-15B, the loading frame described in the present disclosure may be adapted for the beam-bending type test when two adjacent concrete blocks are used. In particular, as seen in FIG. 14A and FIG. 15A, a bottom surface 446 of the first concrete block 411 is connected to a top surface 445 of the second concrete block 413 using a hinge 64. Moreover, further referring to FIG. 14A and FIG. 15A, a front surface 442 of the first concrete block 411 is connected to a front surface 442 of the second concrete block 413 with a FRP test strip 65. As seen in FIG. 14A and FIG. 15A, to provide the FRP test strip 65 a range of motion to bend with the applied load, the first concrete block 411 is positioned on a first support 705 and the second concrete block 413 is positioned on a second support 707, wherein the first support 705 is positioned adjacent a top surface 445 of the first concrete block 411 and pressed against the front surface 442 of the first concrete block 411. The second support 707 is positioned adjacent a bottom surface 446 of the second concrete block 413 and pressed against the front surface 442 of the second concrete block 413. Therefore, as seen in FIG. 14A and FIG. 15A, when the loading frame of the present disclosure is used for the beam-bending type test, the first concrete block 411 and the second concrete block 413 are positioned on the base section 4 using the first support 705 and the second support 707. As described earlier, as seen in FIG. 14A, a load-spreading device 700 may be used to apply the load at the rear surface 444 of the first concrete block 411 and the second concrete block 413, wherein the load-spreading device 700 is positioned in parallel to the loading beam 9. As seen in FIG. 14A, the load-spreading device 700 is in contact with the rear surface 444 of the first concrete block 411 at a first loading point 701. Moreover, as seen in FIG. 14A, the load-spreading device 700 is contact with the rear surface 444 of the second concrete block 413 at a second loading point 703. As seen in FIG. 14A and FIG. 14B, to perform the beam-bending type test for the FRP-concrete bond, a first load, $P_1$, is applied to a bottom surface 117 of the loading beam 9 and a second load, $P_2$, is applied at a mid-point of the load-spreading device 700. The need for external fixed support is eliminated with the use of the load-spreading device 700. The first load and the second load are substantially equal to each other and opposite in direction. The first load and the second load are increased to a bending load, which is the load applied when bond failure occurs in the FRP-concrete bond. Subsequently, the bending load is recorded for the first load and the second load.

Figure 15B:
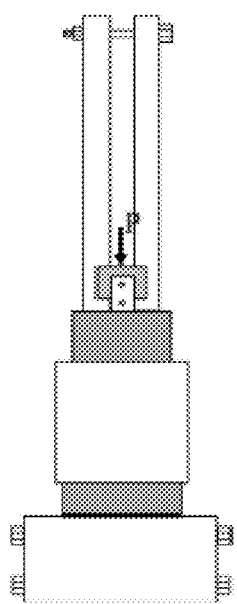
FIG. 15B a front view of the loading frame described in the present disclosure being used for the beam-bending type test, wherein the load is applied using the loading beam of the loading frame.

In another embodiment, as seen in FIG. 15A and FIG. 15B, the loading beam 9 may be used to complete the functionalities of the load-spreading device 700 shown in FIG. 14A. More specifically, the sliding mechanism 11, shown in FIGS. 1-2B, may be used to lower the loading beam 9 to a new height using the plurality of height-adjusting slots 2, shown in FIG. 1 and FIG. 15A, such that the loading beam 9 is in contact with the rear surface 444 of first concrete block 411 and the rear surface 444 of the second concrete block 413 at the first loading point 701 and the second loading point 703 respectively. As seen in FIG. 15A and FIG. 15B, to perform the beam-bending type test for the FRP-concrete bond, a testing load, P, is applied at the top surface 115 of the loading beam 9 such that the loading beam 9 distributes the testing load between the first concrete block 411 and the second concrete block 413. The testing load is increased to cause the FRP-concrete bond to fail.

To conduct double-shear tests, single-shear tests, beam-bending type tests, and tension pull-off tests, the debonding test apparatus 270 of FIG. 16 may be used. See F. M. Mukhtar, "Universal debonding test apparatus for carbon fiber reinforced polymer—concrete system and method for sequential multi-testing," U.S. patent application Ser. No. 16/530,543, incorporated herein by reference in its entirety. When the double-shear test and the mixed-mode test are performed, as shown in FIG. 17A and FIG. 17B respectively, the structural block 27 and the adjustable hanger 29 of the debonding test apparatus 270 are used. As seen in FIG. 17A, a concrete block 40 and a FRP test strip 65 are used in the double-shear test and the mixed-mode test, wherein the FRP test strip 65 creates a U-shaped loop that extends outwards from the concrete block 40. In particular, as seen in FIG. 17A, the U-shaped loop is formed when one end of the FRP strip is attached to a front surface 442 of the concrete block 40 and an opposing end of the FRP strip is attached to a rear surface 444 of the concrete block 40. As illustrated in FIG. 17A, the FRP test strip 65 is positioned around a first positioning cylinder 291, a central block 290, and a second positioning cylinder 293 of the adjustable hanger 29. Furthermore, the FRP test strip 65 is positioned in between a first arm 295 and a second arm 297 of the adjustable hanger 29 shown in FIG. 16.

In another embodiment, as seen in FIG. 17B, the loading frame of the present disclosure may also be used to perform mixed-mode testing using the debonding test apparatus 270 of FIG. 16, wherein shearing and peeling of a FRP-concrete bond is analyzed during mixed-mode testing. As seen in FIG. 17B, an attachment angle, θ, between the FRP test strip 65 and the front surface 442 may be adjusted using the first positioning cylinder 291. Further referring to FIG. 17B, an attachment angle, θ, between the FRP test strip 65 and the rear surface 444 may be adjusted using the second positioning cylinder 293. More specifically, by increasing a distance between the first positioning cylinder 291 and the second positioning cylinder 293, shown in FIG. 17B, the attachment angle between the FRP test strip 65 and the front surface 442, and also the attachment angle between the FRP test strip 65 and the rear surface 444 may be increased. Moreover, by decreasing a distance between the first positioning cylinder 291 and the second positioning cylinder 293, shown in FIG. 17B, the attachment angle between the FRP test strip 65 and the front surface 442, and also the attachment angle between the FRP test strip 65 and the rear surface 444 may be decreased. As seen in FIG. 17B, the first positioning cylinder 291 and the second positioning cylinder 293 may be secured at a first selected slot and a second selected slot from a plurality of angle-adjusting slots 299 shown in FIG. 16 and FIG. 17B. Each of the plurality of angle-adjusting slots 299, shown in FIG. 16, traverses the first arm 295 and the second arm 297. Moreover, further referring to FIG. 16, each of the plurality of angle-adjusting slots 299 is equidistantly positioned along a length of the first arm 295 and the second arm 297. As seen in FIG. 17A and FIG. 17B, for the attachment angle, θ, at the front surface 442 to be equal to the second attachment angle at the rear surface 444, a distance from the central block 290 to the first positioning cylinder 291 is equal to a distance from the central block 290 to the second positioning cylinder 291. As described earlier and as shown in FIG. 18, the adjustable hanger 29, which includes the first positioning cylinder 291, the central block 290, and the second positioning cylinder 293 shown in FIG. 17A, is positioned into the receiving slot 28 formed within the structural block 27.

In one embodiment, as illustrated in FIG. 16, the debonding test apparatus 270 is oriented such that the top surface 272 of the structural block 27 and the top end 107 of the standing guide tower 1 are oriented in the same direction. In another embodiment, as seen in FIG. 21B, the debonding test apparatus 270 may be oriented such that the top surface 272 of the structural block 27 and the top end 107 of the standing guide tower 1 are oriented in opposite directions.

As seen in FIG. 18, the debonding test apparatus 270 is attached to the loading beam 9 with the coupling device 14. Since the receiving slot 28 is rectangular in shape, as seen in FIG. 16 and FIG. 18, the rectangular block 140 is preferably used when attaching the debonding test apparatus 270 to the loading beam 9.

As seen in FIG. 17A and FIG. 17B, when the debonding test apparatus 270 is positioned along the loading beam 9, the concrete block 40, wherein the FRP test strip 65 is attached to the concrete block 40, is secured against the base section 4. As seen in FIG. 18, the pair of rods 24, the holding plate 25, and the pair of rod-receiving slots 8 shown in FIG. 1 may be used to secure the concrete block 40 against the top surface 401 of the base section 4.

As seen in FIG. 17A, to perform the double-shear test for the FRP-concrete bond using the debonding test apparatus 270, a first load, $P_1$, is applied to a bottom surface 117 of the loading beam 9 and a second load, $P_2$, is applied to the top surface 401 of the base section 4. The first load and the second load are substantially equal to each other and opposite in direction. Preferably, the first load and the second load are applied using a hydraulic jack positioned on the base section 4, and in between the standing guide tower 1 and the concrete block 40 shown in FIG. 17A. The first load and the second load are increased to a shear load, which is the load applied when bond failure occurs in the FRP-concrete bond. Subsequently, the shear load is recorded for the first load and the second load.

As seen in FIG. 17B, the test setup used to perform the mixed-mode test, which tests shearing and peeling in the FRP-concrete bond, is similar to the test setup used to perform the double-shear test with the debonding test apparatus 270 as seen in FIG. 17A. However, the FRP test strip 65 is attached to the concrete block 40 at an attachment angle, θ. As shown in FIG. 17B, the attachment angle is determined by positioning of the first positioning cylinder 291 and the second positioning cylinder 293 on the adjustable hanger 29. As seen in FIG. 17B, the first load, $P_1$, is applied to a bottom surface 117 of the loading beam 9 and the second load, $P_1$, is applied to the top surface 401 of the base section 4. The first load and the second load are substantially equal to each other and opposite in direction. Preferably, the first load and the second load are applied using a hydraulic jack positioned on the base section 4, and in between the standing guide tower 1 and the concrete block 40 shown in FIG. 17B. The first load and the second load are increased to a shear-peeling load, which is the load applied when bond failure occurs in the FRP-concrete bond. Subsequently, the shear-peeling load is recorded for the first load and the second load.

Figure 12B:
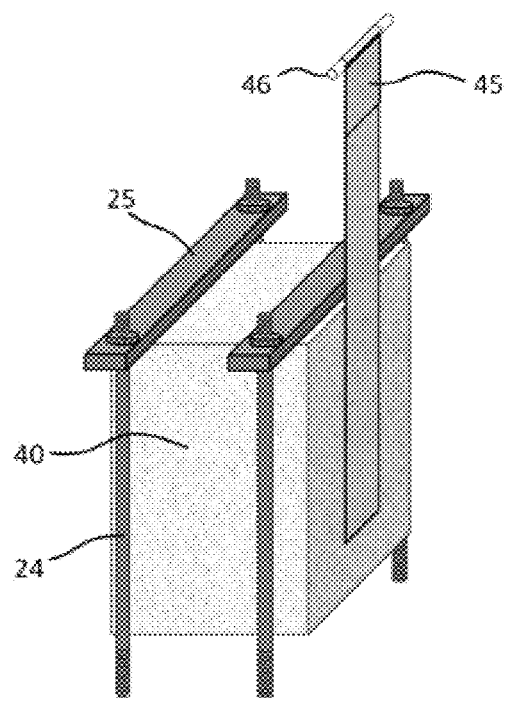
FIG. 12B is a perspective view of an assembly that includes a FRP test strip, a concrete block, a first holding plate, a second holding plate, a first pair of rods, and a second pair of rods in a preferred configuration to reduce a probability of wedge failure during a single-shear test, wherein the first holding plate, the second holding plate, the first pair of rods, and the second pair of rods are used to hold the concrete block against a top surface of the base section.

The loading frame described in the present disclosure may be adapted to perform single-shear testing for a FRP-concrete bond test. More specifically, the single-shear test may be performed by utilizing the attachment plate 32 of the debonding test apparatus 270 shown in FIG. 16. Generally, as seen in FIG. 12B, to perform the single-shear test, the FRP test strip 65 is laterally attached to the concrete block 40 at one end.

Figure 19A:
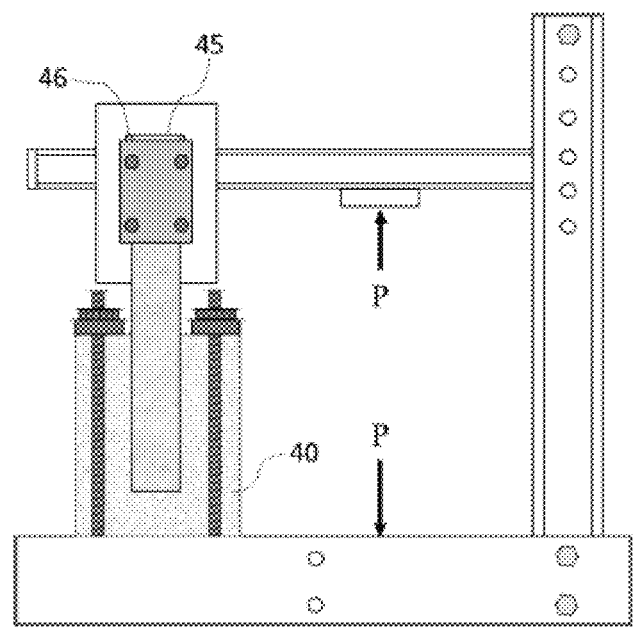
FIG. 19A is a side view of the loading frame described in the present disclosure being used for a single-shear test, wherein a FRP test strip is laterally attached to a structural block of the debonding test apparatus.
Figure 19B:
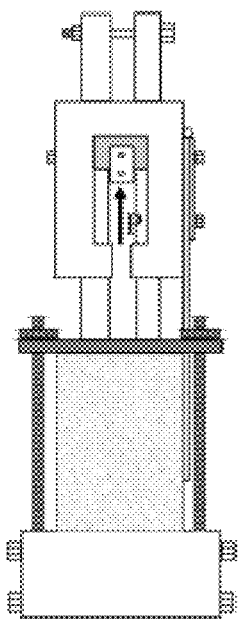
FIG. 19B is a front view of the loading frame described in the present disclosure being used for a single-shear test, wherein a FRP test strip is laterally attached to the structural block of the debonding test apparatus.

When the loading frame described in the present disclosure is used to perform the single-shear test for the FRP-concrete bond, the concrete block 40 is positioned on the base section 4 as shown in FIG. 19A and FIG. 19B. Referring to FIG. 19A, an overlapping free end 45 of the FRP test strip 65, which is opposite to the end connected to the second lateral surface 443, is pressed against the lateral surface 271 of the structural block 27 using the attachment plate 32 and a set of plate-positioning screws 33. In particular, as seen in FIG. 19B, the overlapping free end 45 of the FRP strip is positioned in between the lateral surface 271 of the structural block 27 and the attachment plate 32. To reduce slipping during the single-shear test, as seen in FIG. 19B, the overlapping free end 45 is preferably wrapped around an anchor rod 46, and the anchor rod 46 is connected to the lateral surface 271 of the structural block 27.

Similar to the testing setup used in the double-shear test, as seen in FIG. 19A and FIG. 19B, during the single-shear test, the debonding test apparatus 270 is positioned along the loading beam 9 using the coupling device 14. As illustrated in FIG. 19A, a first load, $P_1$, is applied to a bottom surface 117 of the loading beam 9 and a second load, $P_2$, is applied to the top surface 401 of the base section 4. The first load and the second load are substantially equal to each other and opposite in direction. Preferably, the first load and the second load are applied using a hydraulic jack positioned on the base section 4, and in between the standing guide tower 1 and the concrete block 40 shown in FIG. 19A. The first load and the second load are increased to a shear load, which is the load applied when bond failure occurs in the FRP-concrete bond. Subsequently, the shear load is recorded for the first load and the second load.

The debonding test apparatus 270 of FIG. 16 may be used with a fixed-position loading system to perform direct tension pull-off tests for a FRP-concrete bond. When the debonding test apparatus 270, shown in FIG. 16, is used with the standing guide tower 1, the base section 4, and the loading beam 9, shown in FIG. 1, the loading frame described in the present disclosure may function as a mobile loading system capable of performing the direct tension pull-off tests.

The tension pull-off disk 42 and the top-receiving threaded channel 66 of the debonding test apparatus 270, shown in FIG. 16, are utilized to perform the direct tension pull-off test. As illustrated in FIG. 16, the tension pull-off disk 42 is attached to the structural block 27 with the threaded protrusion 43, wherein the threaded protrusion 43 is positioned into the top-receiving threaded channel 66 and threadably engaged with the plurality of threads 433.

Figure 20:
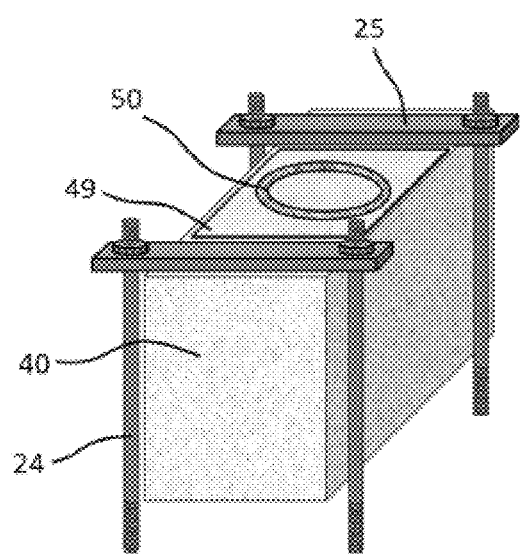
FIG. 20 is a perspective view of an assembly that includes a FRP sheet, a concrete block a first holding plate, a second holding plate, a first pair of rods, and a second pair of rods, wherein the FRP sheet and the concrete block are used with the loading frame described in the present disclosure to perform a direct tension pull-off test, wherein the first holding plate, the first pair of rods, the second holding plate, and the second pair of rods are used to hold the concrete block against the top surface of the base section.
Figure 22:
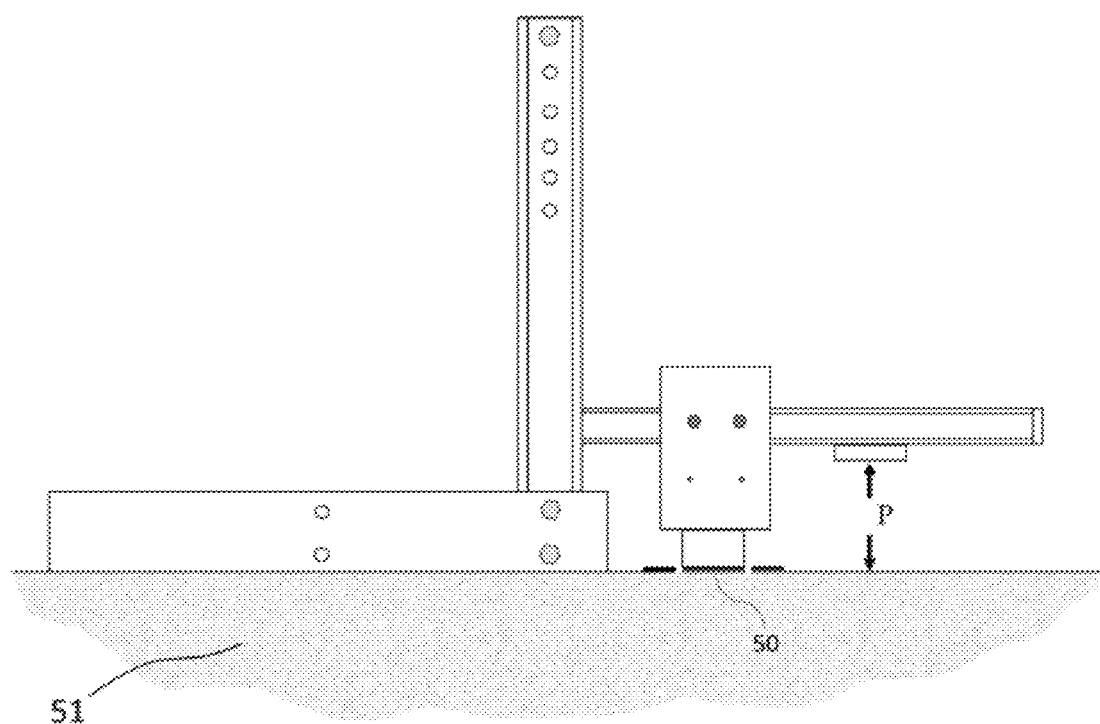
FIG. 22 is a side view of the debonding test apparatus being used for the tension-pull off test, wherein an FRP sheet is layered on a horizontal surface and the loading beam is in the reverse configuration, wherein the standing guide tower is mounted to the base section.
Figure 23:
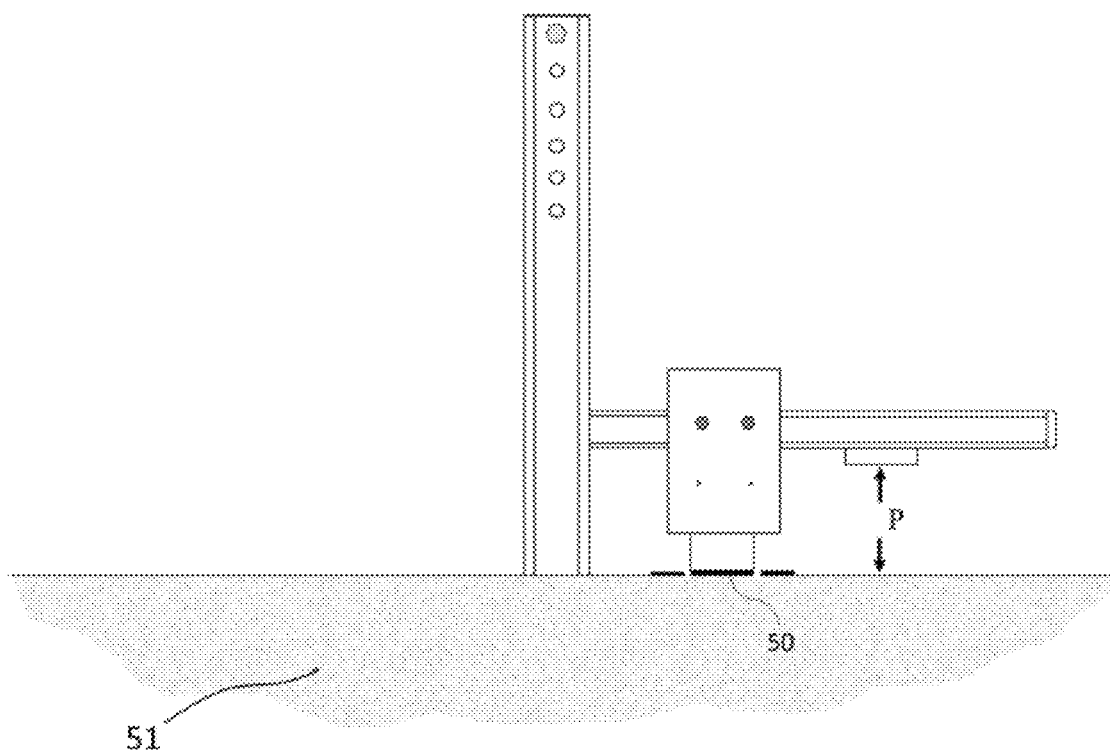
FIG. 23 is a side view of the debonding test apparatus being used for the tension-pull off test, wherein the FRP sheet is layered on the horizontal surface and the loading beam is in the reverse configuration, wherein the standing guide tower is directly mounted to the horizontal surface.

As seen in FIG. 20, the direct tension pull-off test is performed on a FRP test sheet 49 which is bonded to a top surface 445 of a concrete block 40. As further shown in FIG. 20, to separate a circular FRP sheet area 490 of the FRP test sheet 49, which attaches to the tension pull-off disk 42 during the direct tension pull-off test, a circular groove 50 centrally traverses through the FRP test sheet 49 and into the top surface 445 of the concrete block 40. The circular groove 50 separates the circular FRP sheet area 490 from a remainder of the FRP test sheet 49. As seen in FIG. 21A, FIG. 22, and FIG. 23, an area of the circular FRP sheet area 490 is substantially equal to an area of the of tension pull-off disk 42. Therefore, during the direct tension pull-off test, the tension pull-off disk 42, shown in FIG. 16, may be used to remove the circular FRP sheet area 490 in its entirety from the top surface 445 of the concrete block 40 shown in FIG. 20.

To configure the loading frame described in the present disclosure to perform the direct tension pull-off test on the circular FRP sheet area 490 of FIG. 20, the concrete block 40 is held against the base section 4 with a first holding plate 251, a second holding plate 253, a first pair of rods 241, and a second pair of rods 243 as seen in FIGS. 20-21B. In further reference to FIG. 21A and FIG. 21B, the concrete block 40 is placed on the top surface 401 of the base section 4 such that a first terminal 245 end of the first pair of rods 241, shown in FIG. 20, is inserted into the first pair of rod-receiving holes 81 in the base section 4 shown in FIG. 16. As seen in FIG. 20 and FIG. 21A, a second terminal end 247 of the first pair of rods 241 is positioned through the first holding plate 251 to hold the concrete block 40 in between the first holding plate 251 and the base section 4. Similarly, a first terminal end 245 of the second pair of rods 243, shown in FIG. 20, is positioned into the second pair of rod-receiving holes 83 traversing into the base section 4 shown in FIG. 16. As seen in FIG. 20 and FIG. 21A, a second terminal end 247 of the second pair of rods 243 is positioned through the second holding plate 253 to hold the concrete 40 block in between the second holding plate 253 and the base section 4.

As seen in FIG. 21B, to perform the direct tension pull-off test, the debonding test apparatus 270 is positioned along the loading beam 9 using the coupling device 14. However, in contrast to the positioning of the debonding test apparatus 270 on the loading beam 9 during the double-shear test and the single-shear test, the debonding test apparatus 270 is oriented in a flipped configuration during the direct tension pull-off test as seen in FIG. 21B. More specifically, as seen in FIG. 21B, the debonding test apparatus 270 is positioned such that the top surface 272 of the structural block 27 and the top end 107 of the standing guide tower 1 are oriented in opposite directions.

To conduct the direct tension pull-off test, the tension pull-off disk 42 is attached to the circular FRP sheet area 490 as shown in FIG. 21A with an attachment mechanism that may be, but is not limited to, an adhesive layer. Subsequently, further referring to FIG. 21A, a first load, $P_1$, is applied to a bottom surface 117 of the loading beam 9 and a second load, $P_2$, is applied to the top surface 401 of the base section 4. The first load and the second load are substantially equal to each other and opposite in direction as illustrated in FIG. 21A. Preferably, the first load and the second load are applied using a hydraulic jack positioned on the base section 4, and in between the standing guide tower 1 and the concrete block 40. The first load and the second load are increased to a debonding load, which is the load applied when bond failure occurs in the FRP-concrete bond. Subsequently, the debonding load value is recorded for the first load and the second load.

Figure 14B:
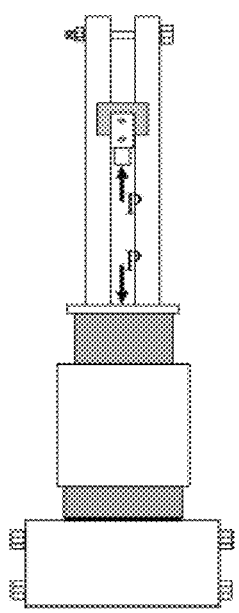
FIG. 14B is a front view of the loading frame described in the present disclosure being used for the beam-bending type test, wherein a load-spreading device is used to distribute a load.

In a different embodiment, the loading frame described in the present disclosure may be used as a mobile loading system when the structural block 27 of the debonding test apparatus 270, shown in FIG. 16, is used independently for beam-bending type tests. More specifically, instead of hingedly connecting the first concrete block 411 and the second concrete block 413, as shown in FIG. 14A and FIG. 14B, the structural block 27 may be hingedly connected to the second concrete block 413 and the load application process may be performed structural block 27 and the second concrete block 413. More specifically, the first concrete block 411 of FIG. 14A may be replaced with the structural block 27, shown in FIG. 19A, FIG. 19B, FIG. 21A, and FIG. 21B. In particular, if a load-spreading device 700 is used as shown in FIG. 14A, a first load, $P_1$, is applied to a bottom surface 117 of the loading beam 9 and a second load, $P_2$, may be applied to the load-spreading device 700 such that the load-spreading device 700 distributes the second load onto the structural block 27 and the second concrete block 413. The need for external fixed support is eliminated with the use of the load-spreading device 700. The first load and the second load are substantially equal to each other and opposite in direction. The first load and the second load are increased to a bending load, which is the load applied when bond failure occurs in the FRP-concrete bond. Subsequently, the bending load is recorded for the first load and the second load.

In another embodiment, as illustrated in FIG. 15A, if the loading beam 9 is used instead of the load-spreading device 700, a testing load, P, is applied at the top surface 115 of the loading beam 9 such that the loading beam 9 distributes the testing load between the structural block 27, shown in FIG. 19A and FIG. 19B, and the second concrete block 413 shown in FIG. 15A. The testing load is increased to cause bending at the FRP-concrete bond.

In a different embodiment, the loading frame described in the present disclosure may be used to apply a load when the debonding test apparatus 270 of FIG. 16 is used for sequential testing, wherein the double-shear test, the single-shear test, the direct tension pull-off test, and the beam-bending type test are sequentially conducted.

The loading frame described in the present disclosure allows the debonding test apparatus 270 of FIG. 16 to perform in situ tension direct pull-off tests as illustrated in FIGS. 22-25. As seen in FIG. 22 and FIG. 23, the debonding test apparatus 270 may be used to perform the direct tension pull-off test on a FRP test sheet 49 that is bonded to a horizontal surface 51. As seen in FIG. 22, the loading beam 9 is in the reversed configuration and the base section 4 is positioned on the horizontal surface 51. In another embodiment, as seen in FIG. 23, the standing guide tower 1 may directly be mounted to the horizontal surface 51.

As seen in FIGS. 21A-24, to conduct the direct tension pull-off test, the tension pull-off disk 42 is attached to the circular FRP sheet area 490 with an attachment mechanism that may be, but is not limited to, an adhesive layer, wherein the circular FRP sheet area 490 is separated by a circular groove 50 traversing into the horizontal surface 51 or the vertical surface 52.

As seen in FIG. 22 and FIG. 23, when conducting in situ direct tension pull-off tests on a horizontal surface 51, a first load, $P_1$, is applied to a bottom surface 117 of the loading beam 9 and a second load, $P_2$, is applied to the horizontal surface 51. The first load and the second load are substantially equal to each other and opposite in direction. Preferably, as illustrated in FIG. 22 and FIG. 23, the first load and the second load are applied using a hydraulic jack positioned on the horizontal surface 51, adjacent the debonding test apparatus 270. The first load and the second load are increased to a debonding load, which is the load applied when bond failure occurs in the FRP-concrete bond. Subsequently, the debonding load value is recorded for the first load and the second load.

Figure 24:
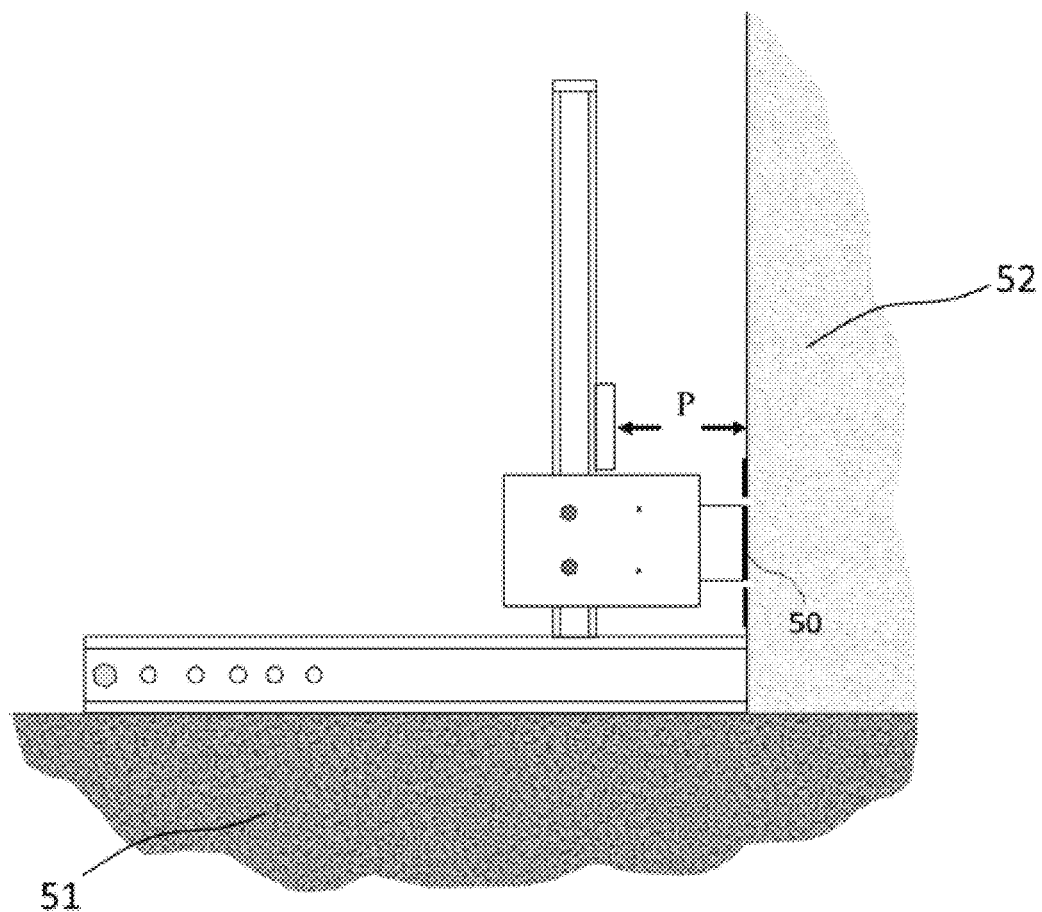
FIG. 24 is a side view of the debonding test apparatus being used for the tension-pull off test, wherein an FRP sheet is layered on a vertical surface and the standing guide tower positioned along a horizontal surface.
Figure 25:
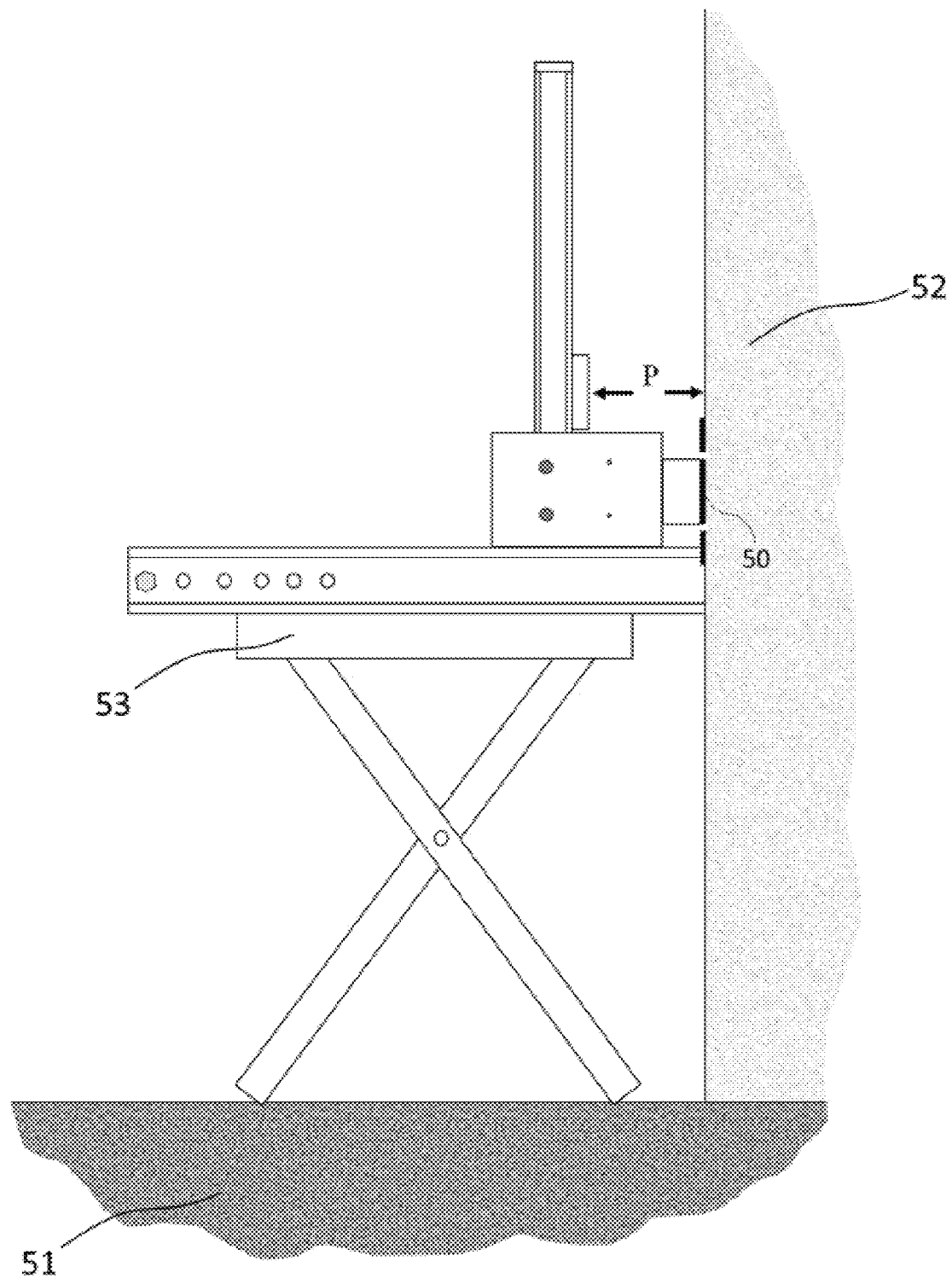
FIG. 25 is a side view of the debonding test apparatus being used for the tension-pull off test, wherein the FRP sheet is layered on a vertical surface which is elevated and the standing guide tower is positioned on a supporting platform.

As seen in FIG. 24 and FIG. 25, the loading frame described in the present disclosure allows the debonding test apparatus 270 to perform in situ direct tension pull-off tests on a FRP test sheet 49 bonded to a vertical surface 52. To conduct the direct tension pull-off test on the vertical surface 52, as seen in FIG. 24, the standing guide tower 1 is pressed against a horizontal surface 51 which is perpendicular to the vertical surface 52. Moreover, the loading beam 9 is adjusted along the standing guide tower 1 such that the tension pull-off disk 42 may be attached to the circular FRP sheet area 490 with an attachment mechanism that may be, but is not limited to, an adhesive layer, wherein the circular FRP sheet area 490 is separated by the circular groove 50 traversing into the vertical surface 52. In further reference to FIG. 24, a first load, $P_1$, is applied to a bottom surface 117 of the loading beam 9 and a second load, $P_2$, is applied to the vertical surface 52. The first load and the second load are substantially equal to each other and opposite in direction. Preferably, the first load and the second load are applied using a hydraulic jack positioned in between the loading beam 9 and the vertical surface 52 shown in FIG. 24. The first load and the second load are increased to a debonding load, which is the load applied when bond failure occurs in the FRP-concrete bond. Subsequently, the debonding load value is recorded for the first load and the second load.

As seen in FIG. 25, if the circular FRP sheet area 490 is elevated, the loading frame is positioned on a supporting platform 53 such that the standing guide tower 1 is pressed against the supporting platform 53. In particular, as seen in FIG. 25, the supporting platform 53, which is preferably height-adjustable, provides a necessary height for the tension pull-off disk 42 to be attached to the circular FRP sheet area 490. When performing the series of FRP-concrete bond tests, for further analysis, data recording devices including, but not limited to, load cells, strain gauges, and linear variable differential transformers (LVDTs) may be used in embodiments of the present disclosure to record data that can be, but is not limited to, loads, strains, and loaded end displacements.

An ideal loading frame may completely transfer an applied load to the FRP-concrete bond. However, due to machine losses, the applied load is not completely transferred to the FRP-concrete bond. The loading frame described in the present disclosure reduces secondary forces that may affect the overall accuracy of results obtained for FRP-concrete bond tests. To improve accuracy, the design of the loading frame distributes the force applied to the loading beam 9 of FIG. 1 during the series of FRP-concrete bond tests. An analysis of the force and the equilibrium of moments may be used to illustrate the reduction in secondary forces resulting from the loading frame of the present disclosure.

Figure 26:
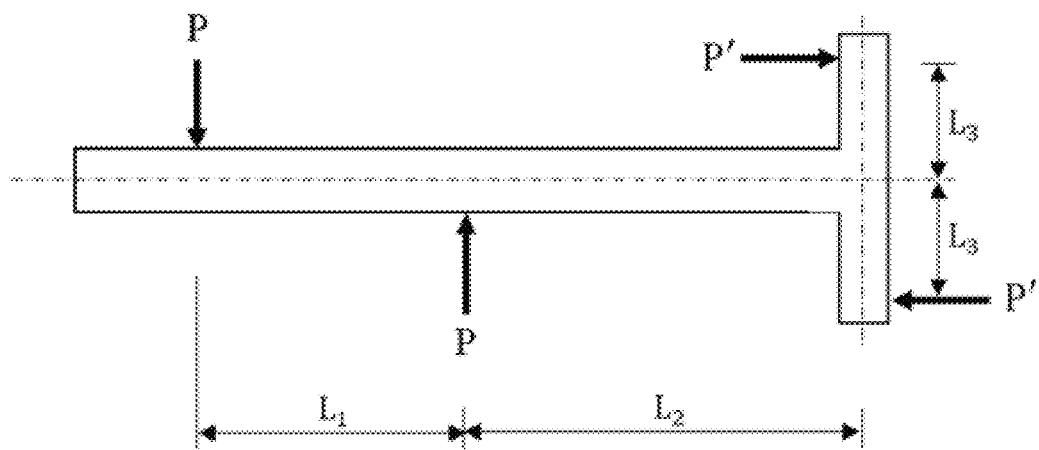
FIG. 26 is a free body diagram of the loading beam, wherein a force distribution during a double-shear test, a mixed-mode test, and a direct tension pull-off test is illustrated.

FIG. 26 illustrates a free body diagram applicable to the loading beam 9 during the double-shear tests, mixed-mode tests, and direct tension pull-off tests. As seen in FIG. 26, a vertical reaction on the loading beam, P, is eliminated by design. From the equilibrium of moments about the sliding end 10 of loading beam 9, equation 1 may be obtained.

$$P' = \frac{P}{2}\left(\frac{L_1}{L_3}\right) \qquad (1)$$

Where:
P'—Horizontal reaction;
P—Vertical reaction;
$L_1$—Moment arm for the vertical reaction;
$L_3$—Moment arm for the horizontal reaction.

From equation 1, the horizontal reaction, P', occurring along the channel 109 configured by the first tower section 101 and the second tower section 103, as shown in FIG. 1, due to the sliding mechanism 11 may be reduced by increasing $L_3$, decreasing $L_1$, or decreasing both $L_1$ and $L_3$ shown in FIG. 26. By reducing the horizontal reactions, which are secondary reactions, the vertical loads/reactions may be dominant. Thus, the overall efficiency of the results obtained for the series of FRP-concrete bond tests may improve.

Figure 27:
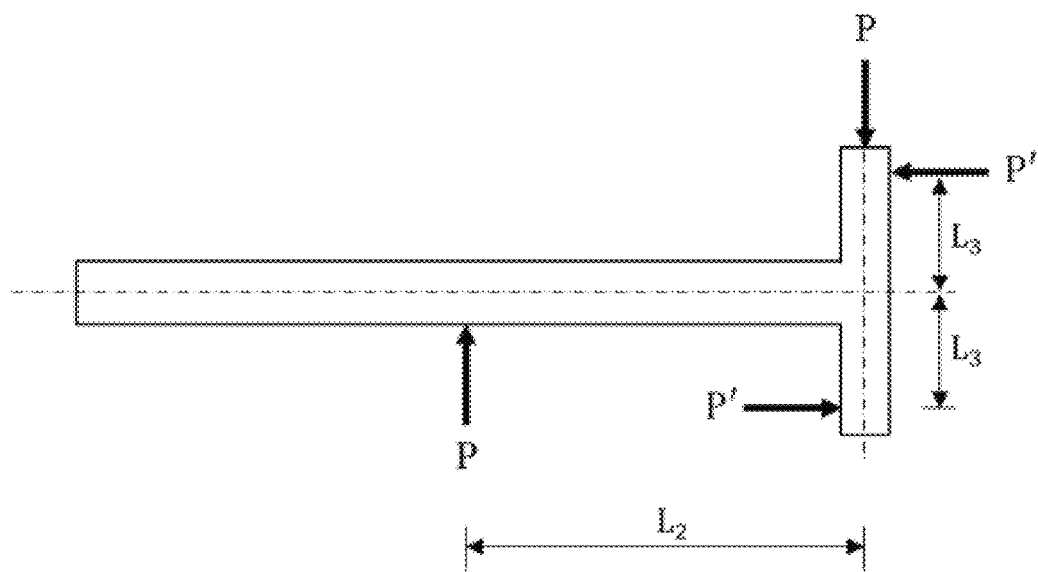
FIG. 27 is a free body diagram of the loading beam, wherein a force distribution during a beam-bending type test is illustrated.

As seen in FIG. 14A and FIG. 14B, to prevent the loading beam 9 from sliding out from the top end 107 of the standing guide tower 1 during the beam-bending type test, the stopping pin 21 is inserted into a slot from the plurality of height-adjusting slots 2. FIG. 27 is a free body diagram illustrating a vertical reaction occurring at the stopping pin 21. Equation 2 may be derived to represent the equilibrium of moments that occur during the beam-bending type test.

$$P' = \frac{P}{2}\left(\frac{L_2}{L_3}\right) \qquad (2)$$

Where:
P'—Horizontal reaction;
P—Vertical reaction;
$L_2$—Moment arm for the vertical reaction;
$L_3$—Moment arm for the horizontal reaction.

From equation 2, the horizontal reaction, P', occurring along the along the channel 109 configured by the first tower section 101 and the second tower section 103 due to the sliding mechanism 11, as shown in FIG. 1, may be reduced by increasing $L_3$, decreasing $L_2$, or decreasing both $L_2$ and $L_3$ shown in FIG. 27.

Figure 28:
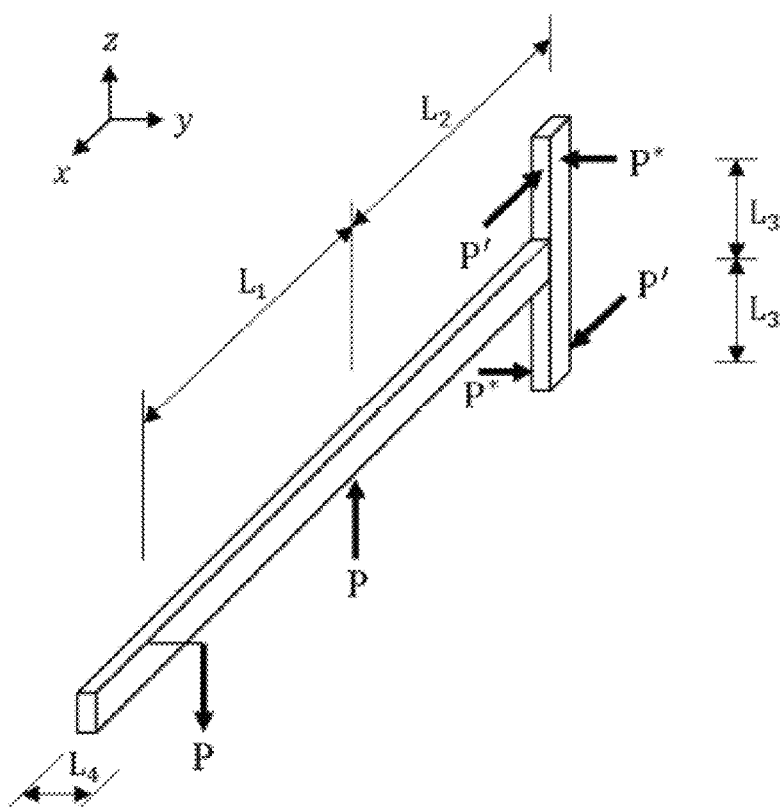
FIG. 28 is a free body diagram of the loading beam, wherein a force distribution during a single-shear test is illustrated.

FIG. 28 is a free body diagram applicable to the loading beam 9, shown in FIG. 19A, wherein the free body diagram is three dimensional when the single-shear test is performed with the debonding test apparatus 270. In reference to FIG. 28, with the presence of $L_4$, a torsional effect may apply to the loading beam 9 of FIG. 19A. Therefore, as shown in FIG. 28, in addition to the horizontal reactions, P' and P*, the torsional effect may also impact the overall results obtained for the FRP-concrete bond. Equation 3 may be derived to represent the equilibrium of moments that occur during the single-shear test.

$$P^* = \frac{P}{2}\left(\frac{L_4}{L_3}\right) \qquad (3)$$

Where:
P'—First horizontal reaction;
P*—Second horizontal reaction;
$L_3$—Moment arm for the horizontal reaction;
$L_4$—Moment arm for the torsional effect.

From equation 3, the second horizontal reaction, P*, which is an external secondary reaction, may be reduced by increasing $L_3$ shown in FIG. 28. Since the debonding test apparatus utilized during the single-shear test has a fixed width, $L_4$ may not be altered to reduce P*.

Figure 29A:
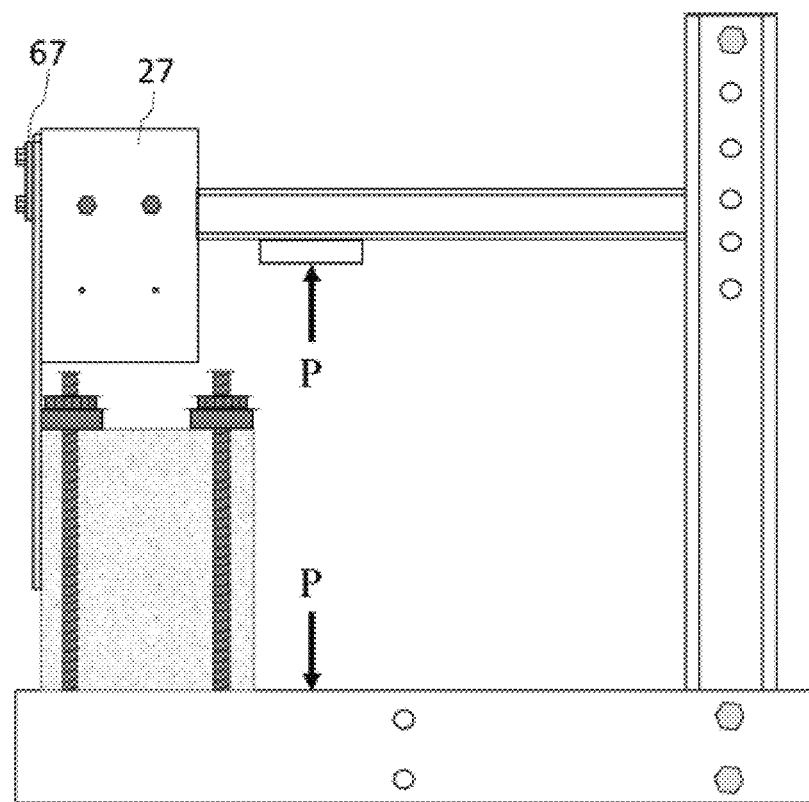
FIG. 29A is a side view of the loading frame described in the present disclosure being used for a single-shear test, wherein the FRP test strip is attached to a leading surface of the structural block.
Figure 29B:
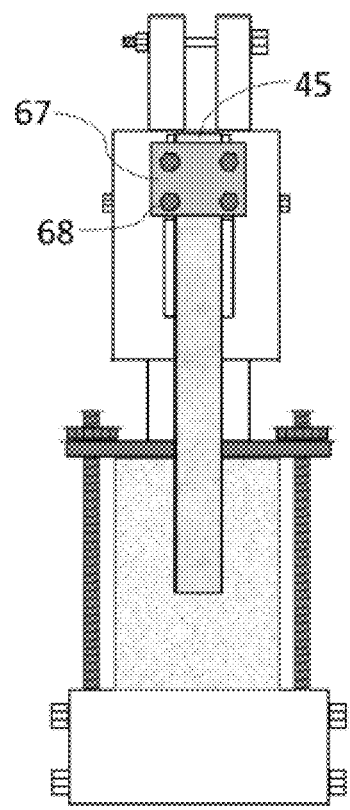
FIG. 29B is a front view of the loading frame described in the present disclosure being used for a single-shear test, wherein a FRP test strip is attached to the leading surface of the structural block.

As described earlier and shown in FIG. 19A and FIG. 19B, during the single-shear test, the FRP test strip 65 is connected to the structural block 27 of the debonding test apparatus 270 using the attachment plate 32, wherein the distance from the loading beam 9 to the FRP test strip 65 results in the torsional effect. To remove the torsional effect, in a different embodiment, as seen in FIG. 29A and FIG. 29B, a secondary attachment plate 67 may be detachably attached to a leading surface 273 of the structural block 27, wherein the leading surface 273 is positioned perpendicular to the lateral surface 271 which is generally used to secure the FRP test strip 65 during the single-shear test.

To hold the overlapping free end 45 of the FRP test strip 65 against the leading surface 273, the secondary attachment plate 67 may be attached to the leading surface 273 using an attachment mechanism that may be, but is not limited to, a set of secondary plate-positioning screws 68. Preferably, as seen in FIG. 29A and FIG. 29B, the set of secondary plate-positioning screws 68 is positioned through the secondary attachment plate 67 and into the coupling device 14 that engages the debonding test apparatus 270 to the loading beam 9.

Figure 30:
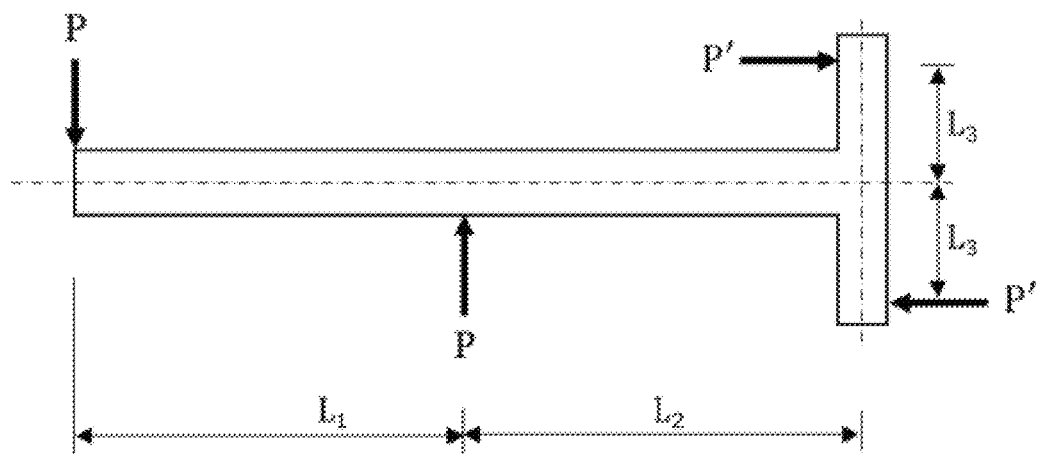
FIG. 30 is a free body diagram of the loading beam, wherein a force distribution during the single-shear test is illustrated, wherein the FRP test strip is attached to the leading surface.

FIG. 30 is a free body diagram corresponding to the testing setup when the secondary attachment plate 67 is used, and is similar to the free body diagram shown in FIG. 26. From the equilibrium of moments about the sliding end 10 of loading beam 9, shown in FIG. 1, equation 1 may be derived for the single-shear test. The horizontal reaction, P', occurring along the channel 109 configured by the first tower 101 section and the second tower section 103 due to the sliding mechanism 11, shown in FIG. 1, may be reduced by increasing $L_3$, decreasing $L_1$, or decreasing both $L_1$ and $L_3$ shown in FIG. 30.

Figure 31:
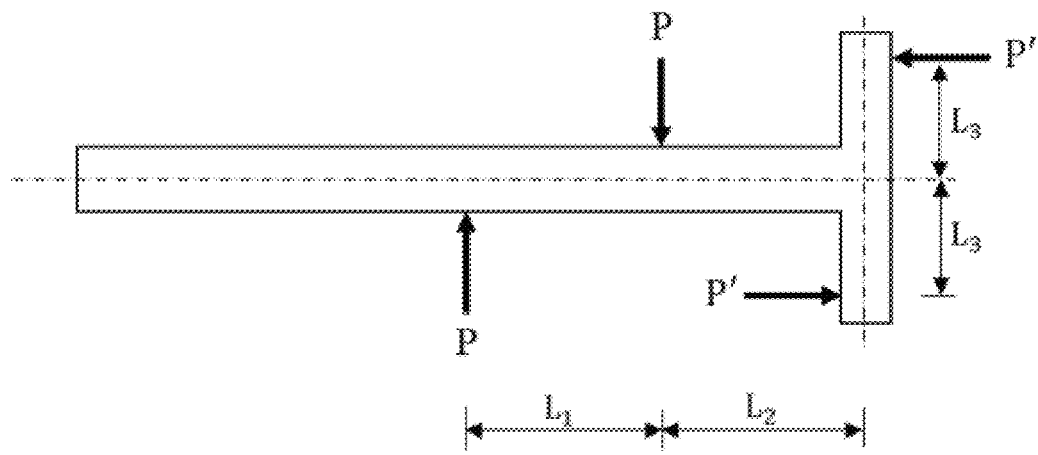
FIG. 31 is a free body diagram of the loading beam, wherein a force distribution during an in situ direct tension pull-off test is illustrated.

A free body diagram applicable to the loading beam 9, shown in FIGS. 21A-25, during the direct tension pull-off tests is illustrated in FIG. 31. Further referring to FIGS. 21A-25, from the equilibrium of moments about the sliding end 10 of loading beam 9, equation 1 may be derived for the direct tension pull-off test. The horizontal reaction, P', occurring along the channel 109, shown in FIG. 1, due to the sliding mechanism 11, shown in FIGS. 1-2B, may be reduced by increasing $L_3$, decreasing $L_1$, or decreasing both $L_1$ and $L_3$ shown in FIG. 31.

In a different embodiment, the moment arm during load application may also be manipulated by positioning the first tower section 101 and the second tower section 103 into the second pair of tower-receiving slots 503 shown in FIG. 1 and FIGS. 7A-7C.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

Obviously, numerous modifications and variations of the present invention are possible in light of the above teachings. It is therefore to be understood that within the scope of the appended claims, the invention may be practiced otherwise than as specifically described herein.

The invention claimed is:

1. A frame and test system for fiber reinforced polymer (FRP)-concrete bond tests, comprising:
   a standing guide tower to adjust a height for one or more fiber reinforced polymer (FRP)-concrete bond tests, wherein the standing guide tower comprises a first tower section and a second tower section;
   a base section having a rectangular shape, wherein the base section comprises a first pair of tower-receiving slots to receive the standing guide tower, wherein the first pair of tower-receiving slots traverses through a top surface of the base section adjacent a first end of the base section;
   the standing guide tower being perpendicularly mounted into the base section and is removably positioned into the first pair of tower-receiving slots, wherein a bottom end of the first tower section is positioned into a first slot of the first pair of tower-receiving slots and a bottom end of the second tower section is positioned into a second slot of the first pair of tower-receiving slots;
   a loading beam to apply a load required in each of the FRP-concrete bond tests, wherein the loading beam comprises a sliding end and a free end, wherein the sliding end of the loading beam is slidably positioned into a channel configured in between the first tower section and the second tower section with a sliding mechanism; and
   wherein a long dimension of the base is substantially the same as a length of the loading beam.

2. The frame and test system of claim 1, wherein the base section comprising a second pair of tower-receiving slots to receive the standing guide tower, wherein the second pair of tower-receiving slots traverses through the top surface between the first end and a second end of the base section; and
   the standing guide tower being perpendicularly mounted into the base section and is removably positioned into the second pair of tower-receiving slots, wherein the first tower section is positioned into a first slot of the second pair of tower-receiving slots and the second tower section is positioned into a second slot of the second pair of tower-receiving slots.

3. The frame and test system of claim 1, wherein the standing guide tower comprising:
   a plurality of height-adjusting slots, wherein the plurality of height adjusting slots traverses through the first tower section and the second tower section adjacent a top end of the standing guide tower, and
   wherein each of the plurality of height-adjusting slots is equidistantly positioned along the first tower section and the second tower section.

4. The frame and test system of claim 1, wherein the loading beam comprising a plurality of positioning slots, wherein the plurality of positioning slots is equidistantly distributed along a top surface of the loading beam in between the sliding end and the free end.

5. The frame and test system of claim 1, further comprising:
- a first pair of fasteners to secure the first tower section with the base section, wherein the first pair of fasteners is threaded into a first pair of base-traversing fastener holes and a first pair of tower-traversing fastener holes,
- wherein the first pair of base-traversing fastener holes traverses through a first lateral surface of the base section,
- wherein the first pair of tower-traversing fastener holes traverses through the first tower section adjacent the bottom end, and
- wherein the first pair of base-traversing fastener holes is aligned with the first pair of tower-receiving slots.

6. The frame and test system of claim 1, further comprising:
- a second pair of fasteners to secure the second tower section with the base section, wherein the second pair of fasteners is threaded into a second pair of base-traversing fastener holes and a second pair of tower-traversing fastener holes,
- wherein the second pair of base-traversing fastener holes traverses through a second lateral surface of the base section,
- wherein the second pair of tower-traversing fastener holes traverses through the second tower section adjacent the bottom end, and
- wherein the second pair of base-traversing fastener holes is aligned with the first pair of tower-receiving slots.

7. The frame and test system of claim 1, wherein the sliding end is T-shaped, wherein the sliding mechanism comprising:
- a first pair of axial sliding wheels;
- a second pair of axial sliding wheels;
- a first pair of radial sliding wheels;
- a second pair of radial sliding wheels;
- the first pair of radial sliding wheels being rotatably engaged with the first pair of axial sliding wheels, wherein a radial sliding wheel of the first pair of radial sliding wheels is perpendicularly and rotatably positioned into a structural body of an axial sliding wheel of the first pair of axial sliding wheels;
- the second pair of radial sliding wheels being rotatably engaged with the second pair of axial sliding wheels, wherein a radial sliding wheel of the second pair of radial sliding wheels is perpendicularly and rotatably positioned into a structural body of an axial sliding wheel of the second pair of axial sliding wheels;
- the first pair of axial sliding wheels and the first pair of radial sliding wheels being attached to a first lateral surface of the loading beam adjacent the sliding end, wherein each of the first pair of axial sliding wheels is attached with a wheel-holding plate and a set of wheel-holding screws, wherein the set of wheel-holding screws presses the first pair of axial sliding wheels against the wheel-holding plate and the first lateral surface of the loading beam; and
- the second pair of axial sliding wheels and the second pair of radial sliding wheels being attached to a second lateral surface of the loading beam adjacent the sliding end, wherein each of the second pair of axial sliding wheels is attached with a wheel-holding plate and a set of wheel-holding screws, wherein the set of wheel-holding screws presses the second pair of axial sliding wheels against the wheel-holding plate and the second lateral surface of the loading beam.

8. The frame and test system of claim 1, wherein the base section comprising at least one pair of rod-receiving holes, wherein the at least one pair of rod-receiving holes traverses into the top surface of the base section adjacent a second end of the base section;
- a pair of rods, wherein a first terminal end of the pair of rods is positioned into the pair of rod-receiving holes; and
- a holding plate, wherein a second terminal end of the pair of rods is positioned through the holding plate.

9. The frame and test system of claim 1, further comprising:
- a coupling device, wherein the coupling device is positioned along a top surface of the loading beam,
- wherein the coupling device is positioned into a preferred slot from a plurality of positioning slots with a positioning screw, and
- wherein the plurality of positioning slots is equidistantly distributed along the top surface of the loading beam in between the sliding end and the free end.

10. The frame and test system of claim 9, wherein the coupling device is a rectangular block comprising a beam-receiving groove; and
- the rectangular block being positioned along a top surface of the loading beam, wherein the loading beam is positioned into the beam-receiving groove.

11. The frame and test system of claim 9, wherein the coupling device comprising a positioning device and a hollow cylinder;
- the positioning device being positioned along a top surface of the loading beam; and
- the positioning device being perimetrically sleeved by the hollow cylinder, wherein the hollow cylinder is removably attached to the positioning device.

12. The frame and test system of claim 9, wherein the coupling device is a semi-cylindrical device comprising a beam-receiving groove; and
- the semi-cylindrical device being positioned along a top surface of the loading beam, wherein the loading beam is positioned into the beam-receiving groove.

13. The frame and test system of claim 1, further comprising:
- a first clamping device, wherein the first clamping device comprises an attachment protrusion,
- wherein the free end of the loading beam is inserted into the attachment protrusion of the first clamping device,
- wherein the loading beam comprises a plurality of positioning slots,
- wherein the attachment protrusion of the first clamping device is engaged to a preferred slot from a plurality of positioning slots;
- a second clamping device, wherein the second clamping device comprises an attachment protrusion,
- wherein the attachment protrusion of the second clamping device is pressed against the top surface of the base section with a holding plate and a pair of clamp-securing rods,
- wherein a first end of the pair of clamp-securing rods is positioned into a pair of rod-receiving holes;
- wherein the pair of rod-receiving holes traverses a top surface of the base section adjacent a second end of the base section; and
- wherein the holding plate is attached to a second end of the pair of clamp-securing rods.

14. The frame and test system of claim 1, further comprising:
- a debonding test apparatus, wherein the debonding test apparatus comprises a structural block having a receiving slot formed therein and an adjustable hanger, wherein the debonding test apparatus is removably attached to the loading beam;
- the adjustable hanger being positioned into the receiving slot adjacent a bottom end of the receiving slot; and
- a coupling device being positioned into the receiving slot adjacent a top end of the receiving slot, wherein the coupling device is positioned along the top surface of the loading beam.

15. The frame and test system of claim 14, wherein the debonding test apparatus further comprises an attachment plate, wherein the attachment plate is attached to a lateral surface of the structural block.

16. The frame and test system of claim 14, wherein the debonding test apparatus further comprises a tension pull-off disk and a top-receiving threaded channel;
- the top-receiving threaded channel centrally traversing into a top surface of the structural block; and
- a threaded protrusion of the tension pull-off disk being positioned into the top-receiving threaded channel, wherein the threaded protrusion is threadably engaged with a plurality of threads internally distributed within the top-receiving threaded channel.

17. The frame and test system of claim 1, wherein the loading beam is in a forward configuration.

18. The frame and test system of claim 1, wherein the loading beam is in a reverse configuration.

19. The frame and test system of claim 1, wherein a cross-section of the first tower section and the second tower section is C-shaped.

* * * * *